US007871772B2

(12) United States Patent
Vodyanoy et al.

(10) Patent No.: US 7,871,772 B2
(45) Date of Patent: *Jan. 18, 2011

(54) METHODS FOR DETECTING MISFOLDED PROTEINS IN BIOLOGICAL SAMPLES

(75) Inventors: Vitaly J. Vodyanoy, Auburn, AL (US); Alexandre M. Samoylov, Auburn, AL (US); Oleg M. Pustovyy, Auburn, AL (US)

(73) Assignee: Auburn University, Auburn, AL (US)

( * ) Notice: Subject to any disclaimer, the term of this patent is extended or adjusted under 35 U.S.C. 154(b) by 192 days.

This patent is subject to a terminal disclaimer.

(21) Appl. No.: 11/601,423

(22) Filed: Nov. 16, 2006

(65) Prior Publication Data

US 2007/0128642 A1    Jun. 7, 2007

Related U.S. Application Data

(63) Continuation of application No. 10/674,750, filed on Sep. 30, 2003, now Pat. No. 7,138,255.

(60) Provisional application No. 60/415,108, filed on Sep. 30, 2002.

(51) Int. Cl.
*C12Q 1/68* (2006.01)
(52) U.S. Cl. .............................. 435/6; 435/7.1; 530/350
(58) Field of Classification Search ....................... None
See application file for complete search history.

(56) References Cited

U.S. PATENT DOCUMENTS

| 5,143,837 | A | 9/1992 | Soya et al. |
| 5,874,238 | A | 2/1999 | Potempa et al. |
| 6,036,774 | A | 3/2000 | Lieber et al. |
| 7,138,255 | B2 | 11/2006 | Vodyanoy et al. |
| 2007/0122799 | A1 | 5/2007 | Vodyanoy et al. |

FOREIGN PATENT DOCUMENTS

| WO | 96/37282 A1 | 11/1996 |
| WO | 9853849 | 12/1998 |
| WO | 02073210 | 9/2002 |
| WO | WO 02/073210 A | 9/2002 |

OTHER PUBLICATIONS

Shaked et al. Journal of Virology, vlo. 75, No. 17, pp. 7872-7874, 2001.*
Lisiecki et al. Journal of Molecular Liquids, vol. 72, pp. 251-261, 1997.*
Houston et al. The Lancet, vol. 356, pp. 999-1000, Sep. 16, 2000.*
Aguzzi, A., "Prion diseases, blood and the immune system: concerns and reality", Haematologica, 2000, vol. 85, No. 1, pp. 3-10.
Aguzzi, A., "Blood simle prion diagnostics", Nature Medicine, 2001, vol. 7, No. 3, pp. 289-290.
Aiken III, J.D. and Finke, R.G., "A Review of Modern Transition-Metal Nanoclusters: Their Synthesis, Characterization, and Applications in Catalysis," Journal of Molecular Catalysis A: Chemical, 1999, vol. 145, Elsevier Science B.V., pp. 1-44.
Attwood, T.K., "Metals in Prion Disease," Trends in Biotechnology, 2002, vol. 20, No. 6, p. 235.
Binns, C. et al, "Synchrotron radiation studies of mass-selected Fe nanoclusters deposited in situ", The European Physical Journal D, 2001, vol. 16, pp. 189-192.
Brown, Paul et al, "Blood infectivity and the prospects for a diagnostic screening test in Creutzfeldt-Jakob disease", J. Lab. Clin. Med., 2001, vol. 137, Mosby Inc., pp. 5-13.
Bush, A.I., "Metals and neuroscience", Current Opinions in Chemical Biology, 2000, vol. 4, Elsevier Science Ltd., pp. 184-191.
Bush, A.I. et al, "Rapid Induction of Alzheimer A beta Amyloid Formation by Zinc", Science, 1994, vol. 265, No. 5177, pp. 1464-1467/.
Bush, A.I., "Metal complexing agents as therapies for Alzheimer's disease", Neurobiology of Aging, 2002, vol. 23, Elsevier Science Inc., pp. 1031-1038.
Campbell, A., et al, "Mechanisms by which metals promote events connected to neurodegenerative diseases", Brain Resaerch Bulletin, 2001, vol. 55, No. 2, Elsevier Sceince Inc., pp. 125-132.
Carrell, R.W. and Lomas, D.A., "Conformational disease", Lancet, 1997, vol. 350, pp. 134-138.
Gerner, C., "Biochemische Analyse endobiontischer Strukuren aus dem menschlichen Blut", [Biochemical Analysis of Endobiontic Structures from Human Blood], Curriculum Oncologicum 01, Jan. 7, 2991, pp. 6-12.
Haritani M. et al, "Hydrated autoclave pretreatment enhancement of prion protein immunoreactivity in formalin-fixed bovine spongiform encephalopathy-affected brain", Acta Neuropathol, 1994, vol. 87; pp. 86-90.
Harper, J.D. and Lansbury Jr., P.T., "Models of Amyloid Seeding in Alzheimer's Disease and Scrapie: Mechanistic Truths and Physiological Consequences of the Time-Dependent Solubility of Amyloid Proteins", An.. Rev. Biochem., 1997, vol. 66, Annual Reviews Inc., pp. 385-407.
Krasemann, S. et al, Induction of antibodies against human prion proteins (PrP) by DNA-mediated immunization of PrP0/0 mice; Journal of Immunological Methods, 1996, vol. 199, pp. 109-118.
Lehmann, S., "Metal ionis and prion diseases", Current Opinion in Chemical Biology, 2002, vol. 6, Elsevier Science Ltd., pp. 187-192.
Liu, C. and Xu, H., "The metal site as a template for the metalloprotein structure formation", Journal of Inorganic Biochemistry, 2002, vol. 22, Elsevier Science B.V., pp. 77-86.
Makeig, S., "Response: Event-related brain dynamics-unifying brain electrophysiology", Trends in Neuosciences, Aug. 2002, vol. 25, No. 8, pp. 390.

(Continued)

*Primary Examiner*—Hope A Robinson
(74) *Attorney, Agent, or Firm*—Andrus, Sceales, Starke & Sawall, LLP

(57) ABSTRACT

Compositions and methods for the isolation and manipulation of misfolded, or partially misfolded, proteins present in blood and other biological materials are provided. In one aspect of the invention, the compositions, hereinafter termed "proteons" are comprised of misfolded proteins. Also provided are compositions and methods for the isolation and manipulation of proteon nucleation centers (PNCs) upon which the proteons of the present in blood and other biological materials form. In another aspect of the invention, the PNCs are comprised of metallic nanoclusters.

17 Claims, 4 Drawing Sheets

OTHER PUBLICATIONS

Otvos, J.D. et al, "Structure of the metal clusters in rabbit liver metallothionein", Proc. Natl. Acad. Sci. USA; Dec. 1980, vol. 77, No. 18, pp. 7094-7098.

Rhoades, E. et al, "Aggregation of an amyloidogenic fragment of human islet amyloid polypeptide", Biochimica et Biophysica Acta, 2000, vol. 1476, pp. 230-238.

Saborio G.P. et al, "Sensitive detection of pathological prion protein by cyclic amplification of protein misfolding", Nature, 2001, vol. 114, pp. 810-813.

Soto, C. et al, "Cyclic Amplification of Protein Misfolding: Application to Prion-Related Disorders and Beyond," Trends in Neurosciences, 2002, vol. 25, No. 8, pp. 390-394.

Thackray, Alan M. et al, "Metal Imbalance and compromised antioxidant function are early changes in prior disease", Biochem. J., 2002, vol. 362, pp. 253-258.

Watanabe, K. et al, "Inhibition against Heat Coagulation of Ovotransferrin by Ovalbumin Dry-Heated at 120 Degree C", J. Agric. Food Chem., 2000, vol. 48, pp. 3965-3972.

Saborio Gabriela et al. (2001)"Sensitive Detection of Pathological Prion Protein by Cyclic Amplification of Protein Misfolding" Nature, Nature Publishing Group, London GB, vol. 411, No. 6839.

Rataboul et al. (2002)"Synthesis and Characterization of Monodisperse Zinc and Zinc Oxide Nanoparticles from the Organmetallic Precursor [Zn(C6H11)2]" Journal of Organometallic Chemistry, Elsevier-Sequoia S.A. Lausanne, CH, vol. 643-644.

Rivas et al. (1993) "First Steps Towards Tailoring Fine Andultrafine Iron Particles Using Microemulsions," IEE Transactions on Magnetics, IEEE Service Center, New York, NY, US, vol. 29, No. 6.

Kapoor et al. (2000)"Laser-induced fragmentation and melting of cadmium and copper nanoparticles" Materials Research Bulletin, Elsevier, Kidlington, GB, vol. 35, No. 13.

(1997) "In-situ Observations of Classical Grain Growth Mechanisms During Sintering of Copper Nanoparticles on (001) Copper," Applied Physics Letters, AIP, American Institute of Physics, Melville, NY, US, vol. 71, No. 12.

Enderlein, Gunther (Prof., Dr.), "Bacteria Cyclogeny", pp. 27-39; published in German 1916, 1981 (translated Jan. 1999).

Ursini, Fulvio, et al, "Atherosclerosis: Another Protein Misfolding Disease?", TRENDS in Molecular Medicine, vol. 8, No. 8, pp. 370-374, Aug. 2002.

Wetterberg, Lennart, et al "Micrometer-Sized Particles in Cerebrospinal Fluid (CSF) in Patients with Schizophrenia", Neuroscience Letters, 329 (2002) pp. 91-95.

Schluter, Karen and Drenckhahn, Detlev, "Co-Clustering of Denatured Hemoglobin with Band 3: Its Role in Binding of Autoantibodies Against Band 3 to Abnormal and Aged Erythrocytes", Medical Sciences, Proc. Natl. Acad. Sci. USA, vol. 83, pp. 6137-6141, Aug. 1986.

Prusiner, Stanley B., "Molecular Biology of Prion Diseases", Science, vol. 252, Jun. 14, 1991, pp. 1515-1522.

Soto, Claudio, "Protein Misfolding and Disease; Protein Refolding and Therapy", FEBS Letters, 498 (2001) pp. 204-207.

Wille, Holger, et al, "Structural Studies of the Scrapie Prion Protein by Electron Crystallography", PNAS, vol. 99, No. 6, Mar. 19, 2002, pp. 3563-3568.

Geschwind, Michael D. (M.D., Ph.D.), et al, "Challenging the Clinical Utility of the 14-3-3 Protein for the Diagnosis of Sporadic Creutzfeldt-Jakob Disease", Arch Neurol, vol. 60, Jun. 2003, pp. 813-816.

Kannan, Rama, et al, "Isolation and Characterization of the Hemichrome-Stabilized Membrane Protein Aggregates from Sickle Erythrocytes", The Journal of Biological Chemistry, vol. 263, No. 27, Issue of Sep. 25, 1988, pp. 13766-13773.

Jaikaran, Emma T. A. S. and Clark, Anne, "Islet Amyloid and Type 2 Diabetes: From Molecular Misfolding to Islet Pathophysiology", Biochimica et Biophysica Acta, 1537 (2001) pp. 179-203.

Rahman, Qamar, et al, "Evidence That Ultrafine Titanium Dioxide Induces Micronuclei and Apoptosis in Syrian Hamster Embryo Fibroblasts", Environmental Health Perspectives, vol. 110, No. 8, Aug. 2002, pp. 797-800.

Wille, Holger, et al, "Structural Studies of the Scrapie Prion Protein by Electron Crystallography", Biophysical Journal, vol. 82, Issue 1, p. 169A, Part 2 Meeting; Abstract, p. 825, published Jan. 2002.

Dyson, H. Jane, "Structure and Dynamics of Prion and Doppel Proteins", Biophysical Journal, vol. 82, Issue 1, p. 169A, Part 2 Meeting; Abstract, p. 824, published Jan. 2002.

* cited by examiner

METHODS FOR DETECTING MISFOLDED PROTEINS IN BIOLOGICAL SAMPLES

CROSS REFERENCE TO RELATED APPLICATION

This application claims the benefit of U.S. application Ser. No. 10/674,750 filed on Sep. 30, 2003, which claims the benefit of U.S. Provisional Application Ser. No. 60/415,108 filed on Sep. 30, 2002, which is hereby incorporated in its entirety by reference herein.

FIELD OF THE INVENTION

The present invention relates generally to compositions and methods for the isolation and manipulation of misfolded proteins and their nucleation centers.

BACKGROUND OF THE INVENTION

There are many disorders that are thought to arise form the same general mechanism based upon misfolding and aggregation of underlying proteins, including prion-related disorders, neurodegenerative diseases, and several systematic disorders. See, for example, Schluter et al. (1986) *PNAS* 83:6137-6141; Kannan et al. (1988) *J. Biol Chem.* 263:3766-13773; Carrell and Lomas (1997) *Lancet* 350:134-138; Carrell and Gooptu (1998) *Curr. Op. Struc. Biol.* 8:799-809; Soto (2001) *FEBS Letters* 498:204-207; Jaikaran and Clark (2001) *Biochimica et Biophysica Acta* 1537:179-203; Ursini et al. (2002) *Trends Mol. Med.* 8:370-374; and Davis et al. (2002) *Lancet* 359:2242-2247.

One of the suggested mechanisms of protein aggregation is seeded polymerization, in which initial seeds nucleate the deposition of monomers. For example, aggregates of denatured hemoglobin called Heinz bodies where found in ages erythrocytes. See Schluter et al. (*Supra*). Further, Kannan et al. (*Supra*) described a protein aggregation from sickle erythrocytes that is mostly composed of globin. Particles resembling those described by Enderlein (1925) *Bakterien-Cyclogenie* (Verlag d Gruyter & Co, Berlin), were isolated form the blood of cancer patients and determined to be composed of mainly denatured hemoglobin (Gerner (1997) *Blut. Curr. Onokol.* 7:6P12).

Aggregated proteins associated with disorders are found in other biological materials, as well. For example, proteinaceous particles isolated from brain were identified as causing scrapie (Prusiner (1982) *Science* 216:136-144). Since then, these particles and their structure have represented important areas of study (Prusiner (1991) *Science* 252:1515-1522; Wille et al. (2002) *Biophysical J.* 82:825; Wille et al. (2002) *PNAS* 99:3563-3568; Greschwind et al. (2002) *Neurology* 58:A135-A135; Dyson et al. (2002) *Biophysical J.* 82:824), and methods for the sensitive detection fluid of patients with schizophrenia (Wetterberg et al. (2002) *Neurosci Lett.* 329: 91-5). Accordingly, new compositions and methods for the formation, isolation, and detection of misfolded, aggregated proteins are required.

BRIEF SUMMARY OF THE INVENTION

Compositions and methods for the isolation and manipulation of misfolded, or partially misfolded, proteins present in blood and other biological materials are provided. In one aspect of the invention, the compositions, hereinafter termed "proteons," are comprised of misfolded proteins. Also provided are compositions and methods for the isolation and manipulation of proteon nucleation centers (PNCs), upon which the proteons of the present invention form. The PNCs are comprised of metallic nanoclusters.

Proteons can be visualized by microscopy of biological materials, for example fluids such as blood samples of mammals and homogenates of vegetable matter. As proteons are comprised of misfolded proteins, detection of proteons and identification of proteins can be used to diagnose and measure progression of disease states. For example, proteons isolated and purified from blood and blood plasma lack detectable nucleic acids, but contain two major poly peptide populations with high homology to the alpha chain of hemoglobin. Accordingly, methods for the amplification and detection of misfolded protein in biological sample are provided. Additionally, methods for the clearance of misfolded protein from a sample biological material are provided. The method can be manipulated by subjecting the sample to heat or pressure, or by carrying out various numbers for seeding steps. Methods for amplification include heat and pressure treatment of a sample. Likewise, subjecting a biological sample to or treating it with metal clusters increases the concentration of proteons.

While the present invention is not bound to any particular mode of action, it is believed that proteons are formed by a mechanism involving the reversible polymerization and aggregation of proteins, particularly misfolded proteins, on a nucleation center. For convenience, the nucleation centers are referred to as "proteon nucleation centers" or "PNCs."

The PNCs of the invention are unexpectedly pro-apoptotic when added to cultured animal cells. Accordingly, pro-apoptotic compositions and methods for their production are also provided herein.

BRIEF DESCRIPTION OF THE SEVERAL VIEWS OF THE DRAWING(S)

FIG. 1 shows various electron micrographs of proteons in thin sections. Transmission electron microscopy (TEM) was used to prepare electron microscopy of type proteons. See FIG. 1A and FIG. 1B. Also shown are TEM of type 2 proteons. See FIG. 1A and FIG. 1B. Also shown are TEM of type 2 proteons. See FIG. 1C and FIG. 1D. TEM of negatively stained type 2 proteons are shown in FIG. 1E and FIG. 1F. A electron micrograph of a type 2 proteon prepared using scanning electron microscopy (SEM) is shown in FIG. 1G. Scale bars (in microns): FIG. 1A: 5; FIG. 1B-1F; 0.5; FIG. 1G: 1.

Figure 1:
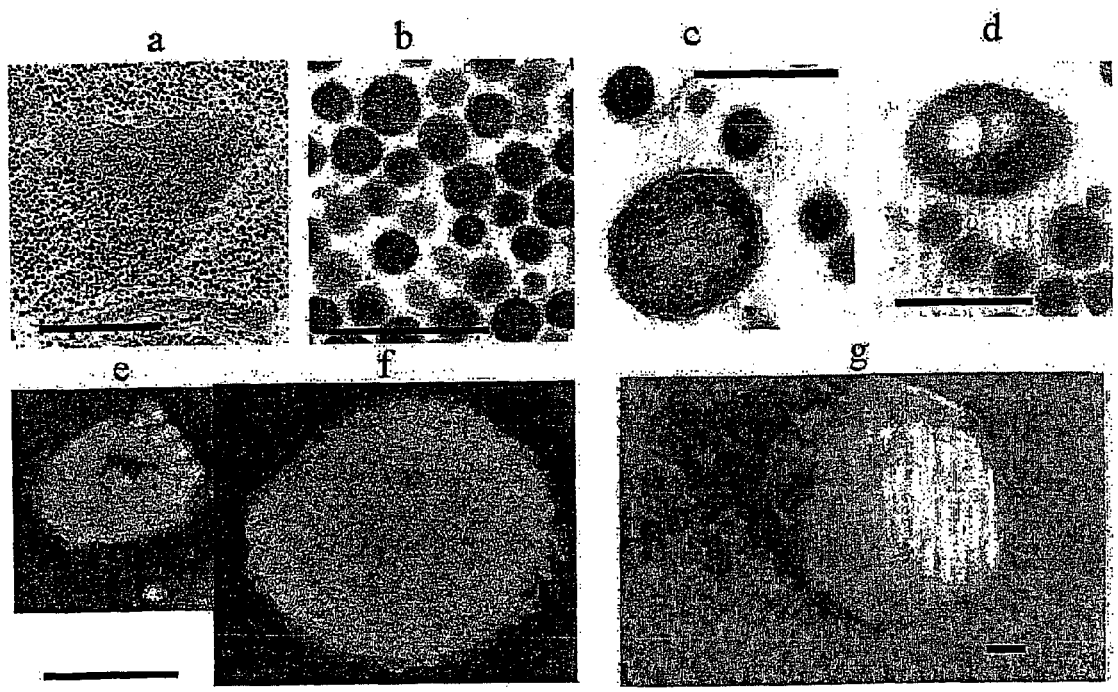
FIG. 1A is an electron micrograph prepared using transmission electron microscopy (TEM) of a type 1 proteon.
FIG. 1B is a TEM electron micrograph of another type 1 proteon.
FIG. 1C is a TEM electron micrograph of a type 2 proteon.
FIG. 1D is a TEM electron micrograph of another type 2 proteon.
FIG. 1E is a TEM electron micrograph of a negatively stained type 2 proteon.
FIG. 1F is a TEM electron micrograph of another negatively stained type 2 proteon.
FIG. 1G is an electron micrograph prepared using scanning electron microscopy (SEM) of a type 2 proteon.

FIG. 4B1 shows a dark filed photomicrograph of brain glioma cells before exposure to PNCs.

Figure 2:
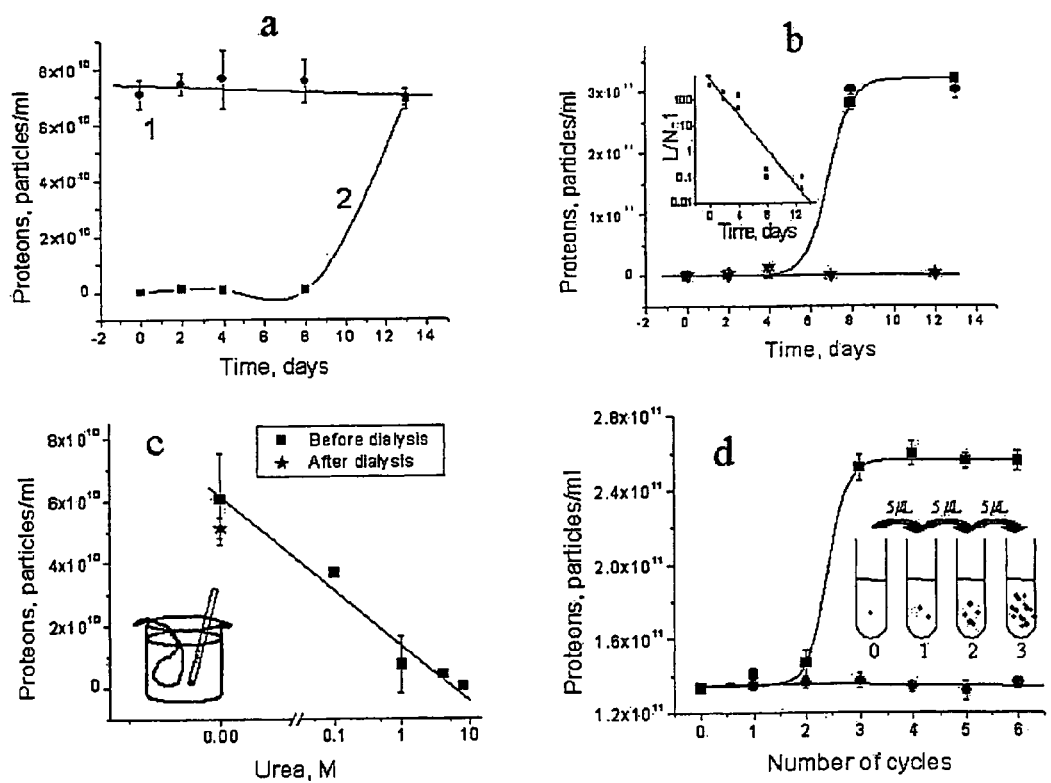
FIG. 2A is a graph illustrating proteon proliferation in purified water and in blood plasma showing the number of proteons visible as a function of time.
FIG. 2B is a graph of proteon proliferation in two different growth mediums showing the number of proteons visible as a function of time.
FIG. 2C is a graph of proteon proliferation in the presence and absence of urea showing the number of proteons visible as a function of urea concentration.
FIG. 2D is a graph illustrating cyclic amplification of proteons in plasma showing the number of proteons visible as a function of the number of amplification cycles.

FIG. 4B2 shows a dark field photomicrograph of brain glioma cells after exposure to PNCs.

Figure 3:
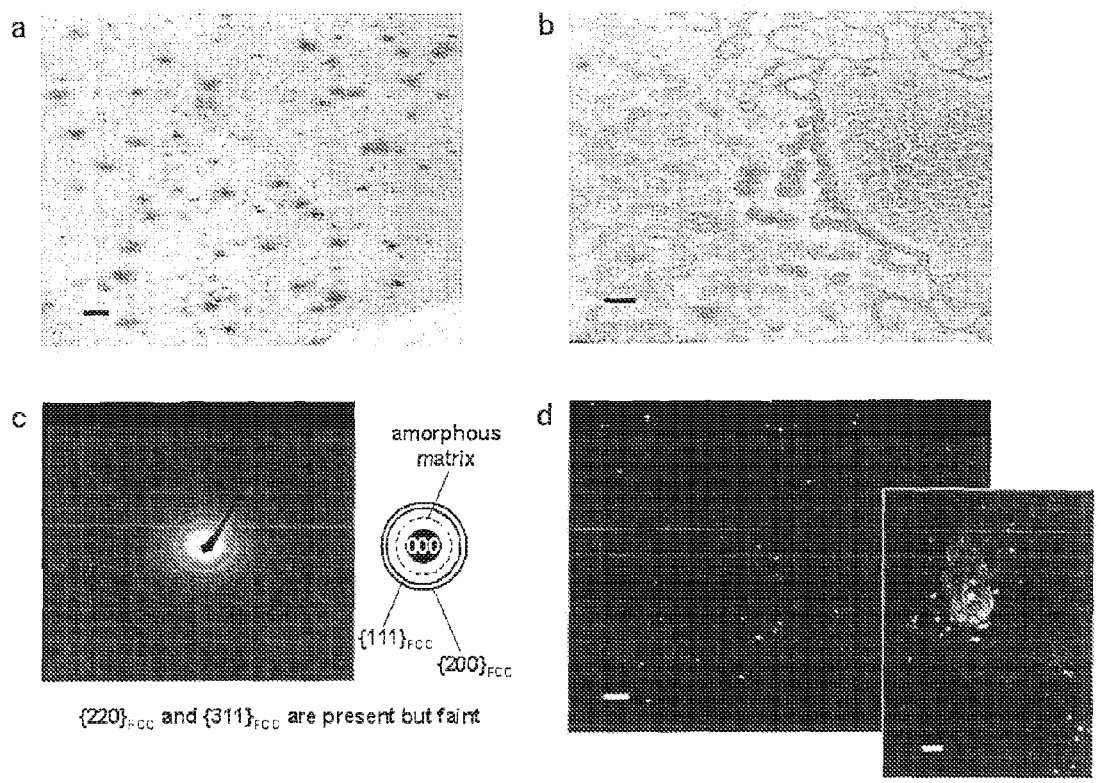
FIG. 3A is a TEM electron micrograph of clusters of crystalline, metallic copper nanoparticles.
FIG. 3B is a TEM electron micrograph of an amorphous matrix for the copper nanoparticles shown in FIG. 3A.
FIG. 3C is a SAD pattern identifying the copper nanoparticles in FIG. 3A.
FIG. 3D is a DF image of copper nanoparticles prepared using a portion of FCC ring of FIG. 3C.

FIG. 4B3 is a dark field photomicrograph of brain glioma cells after exposure to a staurosporine.

Figure 4:
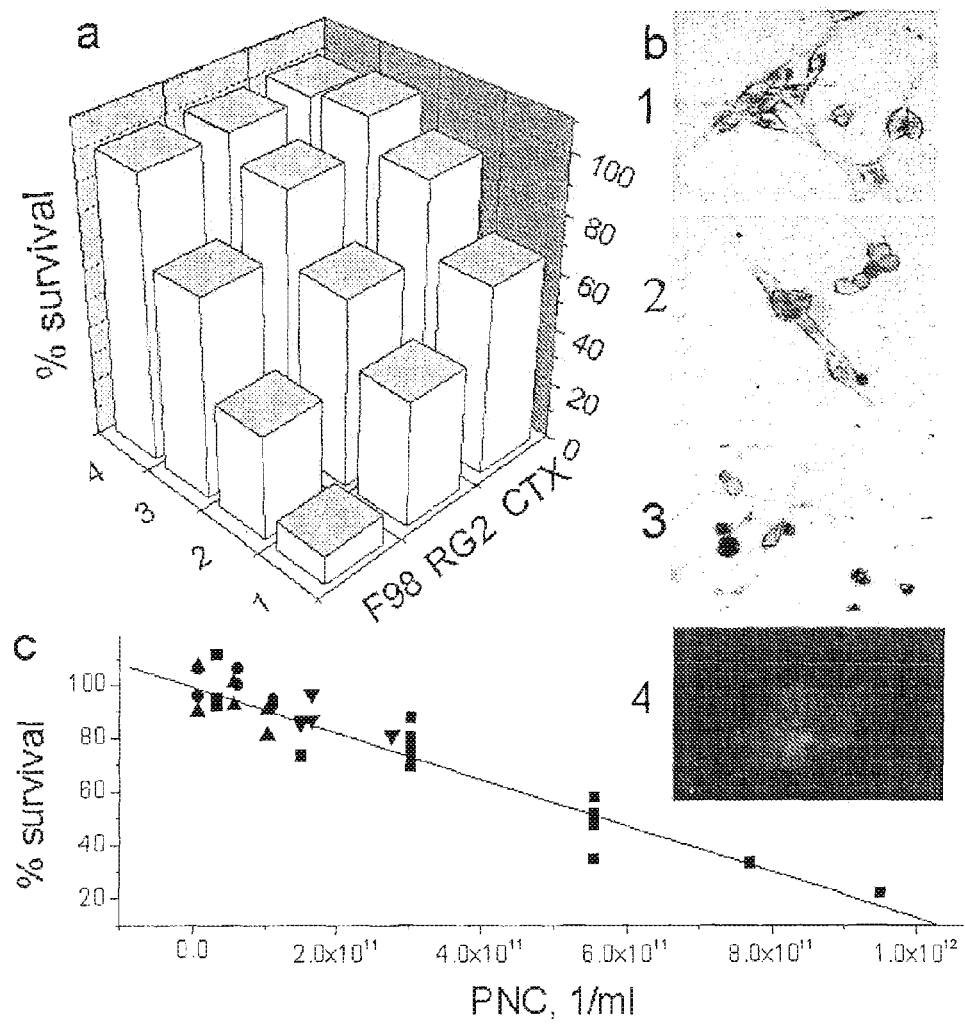
FIG. 4A is a three-dimensional bar graph illustrating the viability of three different cultured cells after exposure to proteon nucleation centers (PNCs) obtained from shark blood at four different concentrations of PNC/ml.

FIG. 4B4 is a fluorescenen photomicrograph of brain glioma cells exposed to PNCs and stained with propidium iodide.

FIG. 4C is a graph illustrating the viability of brain glioma cells obtained from various animals after exposure to PNCs at different concentrations.

DETAILED DESCRIPTION OF THE INVENTION

FIG. 2 shows proliferation of proteons. Proteons in purified water and blood plasma incubated at 37° C. in an atmosphere of ambient air, showing the number of proteons visible in the dark-field microscope as a function of time. See FIG. 2A. Proteons and plasma were incubated in tissue culture media, ■, ●—proteons and plasma in culture growth medium, respectively; ▲, ▼—D5648 and D6429 growth medium, respectively. The insert shows a linear fit of the experimental data to the logistic equation $Ln(L/N-1)=k(T_{1/2}-t)$, where L=maximal number of proteons, N=number of proteons at time t, and $T_{1/2}$=time when N=L/2 (Jarman, 1970). See FIG. 2B. Assembly and disassembly of proteons in the presents of urea is shown in FIG. 2C. After the proteons were assembled in the presence of urea, the urea was then removed from the suspension of proteons by dialysis. Cyclic amplification of proteons in plasma is shown in FIG. 2D. The first sample was incubated for 15 minutes at 65° C. and normal pressure. Treated samples of 5 μL were serially introduced into untreated sample and subjected to a heat cycle, up to 6 cycles.

FIG. 3 shows characterization of Cu nanoparticles using TEM, with a-Fe particles shown for comparison. A BF image showing clusters of crystalline, metallic Cu nanoparticles is shown in FIG. 3A. A BF image of the amorphous matrix is shown in FIG. 3B. A SAD pattern identifying the nanoparticles in FIG. 3A as an FCC phase with a lattice parameter of approximately 360 pm and a random crystallographic orientation is shown in FIG. 3C. Centered DF image prepared using a portion of the {111} FCC ring is shown in FIG. 3D. The nanoparticles appear bright, on a dark background, indicating that the {111} FCC diffraction maxima originated from the nanoparticles and not the matrix (since the Cu particles are randomly oriented, many of the particles are out of contrast). The inset shows clumped and individual a-Fe particles (DF from a portion of the {110} BCC ring). Scale bars shown in FIGS. A, B, and D represent 50 nm. Scale bars in the insert represent 20 nm.

FIG. 4 shows the effect of PNC on cell viability. FIG. 4A shows the viability of cultured cells after 20 hours of exposure to PNC obtained from the shark blood at different concentrations of PNC/ml.: (1) –1.7×10$^{11}$; (2) –9.1×10$^{10}$; (3) –9.9× 10$^9$; (4) –0. (F98, RG2—rat and mouse brain glioma cells respectively, CTX—rat transfected astrocytes). FIG. 4B shows dark-field photomicrographs of the mouse rat glioma cells. FIGS. 4B1 and 4B2 show cells before after exposure to 7.7×10$^{11}$ PNC/ml, respectively. FIG. 4B3 shows cells after exposure to 1.0 μM staurosporine. 4-Fluorescence photomicrograph of RG2 glioma cell exposed to 7.7×10$^{11}$ PNC/ml for 20 h and stained with Annexin V and propidium iodide (400X). FIG. 4C shows viability of RG2 glioma cultured cells after 20 hours of exposure to PNC obtained from the blue shark (*Prionance*) (■), hound dog, (●), human (▲), and New Zealand white rabbit (Harland Sprague Dawley) (▼) blood at different concentrations. R=0.95, p<0.0001.

The present invention now will be described more fully hereinafter with reference to the accompanying drawings, in which some, but not all embodiments of the invention are shown. Indeed, the invention may be embodied in many different forms and should not be construed as limited to the embodiments set forth herein; rather, these embodiments are provided so that this disclosure will satisfy applicable legal requirements.

Compositions and methods for identifying and characterizing disease states are provided. The compositions comprise misfolded proteins aggregated on a nucleation center. The aggregated proteins are referred to herein as proteons. The nucleation centers are referred to as proteon nucleation centers (PNCs).

DEFINITIONS

By "proteons" are intended protein bodies, generally on the order of a few tens of nanometers up to several microns across, comprised of misfolded or partially misfolded proteins surrounding a PNC. In one aspect of the invention, proteons can be isolated from blood, including human, bovine, horse, pig, cat, dog, fish, rabbit, and rat blood. In another aspect of the invention proteons can be isolated from plasma, including human, bovine, horse, pig, cat, dog, fish, rabbit and rat plasma.

By "PNC" is intended the metallic nucleation centers isolated as described herein. In one aspect of the invention, PNCs can be isolated from blood, including human, bovine, horse, pig, cat, dog, fish, rabbit, and rat blood. In another aspect of the invention, PNCs can be isolated from plasma, including human, bovine, horse, pig, cat, dog, fish, rabbit and rat plasma.

By "plasma" is intended the supernatant produced by the centrifugation of blood or other suspension of biological material.

By "seeding" is intended adding an amount of either a PNC or proteon to a biological sample.

The proteons of the invention can be identified and quantified in biological samples. Such samples include serum, blood, other bodily fluids, tissue including brain, other organ tissue and the like. To identify the proteons in tissue, the tissue is homogenized in a fluid or liquid.

Proteons can be isolated from biological samples of any mammal including but not limited to human, primate, bovine, cattle, horse, sheep, pig, cat, dog, rabbit, rat, deer, ox, mouse, and the like. They can also be detected in samples from fish, chicken, turkey, duck, and the like.

As indicated, proteons are comprised of misfolded proteins. In one aspect, the proteon compositions of the invention show an apple-green birefringence when stained with congored. This staining pattern is analogous to that obtained with prions and other amyloid proteins, all of which are included in the class of congophilic proteins. See Kelly (1996) *Curr. Opin. Struct. Biol.* 6:11-17. These proteins are associated with various disorders or disease states. Thus, the identification of proteons comprised of such proteins is indicative of a disorder or disease state. Likewise, the number of proteons in a sample comprised of such proteins is predicative of the progression of the disease. That is, the number of proteons in a sample correlates with progression of a disease state. Therefore, quantification of proteons in a sample is useful for determining or diagnosing the stage of disease or disorder and can help in planning treatments or therapies for the disease. Examples of disorders involving misfolded proteins and the relevant proteins that can be utilized in the methods of the present invention are set forth in Table 1, below. The disorders associated with congophilic proteins are set forth in Table 2, below.

It is recognized that for proper diagnosis, proteons must not only be identified, but also the misfolded protein in the proteons must not only be identified, but also the misfolded protein in the proteon must be identified. Methods for protein purification and identification include antibody binding amino acid sequencing, and the like.

TABLE 1

Conformational diseases. See Carrel and Lomas (1997) Lancet 350: 134-138; Carrell and Gooptu (1998) (1998) Curr. Op. Struc. Biol. 8: 799-809; Soto (2001) FEBS letters 498: 204-207; Jaikaran and Clark (2001); Ursini et al. (2002) Trends Mol. Med. 8: 370-374; Kannan et al. (1988) J. Biol. Chem. 263: 13766-13773; Schluter and Drenckhahn (1986) PNAS 83: 6137-6141; Gerner et al. (2002); Davis et al. (2002) Lancet 359: 2242-2247; Fernandez et al. (2001) Atherosclerosis 158, 103, 111 (atherosclerosis); Papalexis et al. (2001) Mol. Biochem. Parasitology 115: 77-86; Esievo et al. (1984) Veterinary Parasitology 15: 181-185; Igoe et al. (2002) Clin. Microb. Newsletter 24: 69-70; Kreidl et al. (2002) J. Am. Coll. Surgeons 194: 387; Beckers (2001) Netherlands J.. Med 58: 207-207 (autoimmune diseases); Ismeno et al. (1999) Int'l J. Cardiology 69: 179-183; Klibansky et al. (1966) Toxicon 3: 213-216; Siebert et al. (2003) Toxicon 41: 831-839; Szabo et al. (2002) Thrombosis Research 107: 357-363; Kaioumova et al. (2001) Chemosphere 43: 801-805.

| Protein | Disease |
| --- | --- |
| Hemoglobin | Sickle cell anemia and aggregates |
|  | Heinz bodies in ages erythrocytes |
|  | Unstable hemoglobin inclusion body hemolysis |
|  | Drug induced inclusion body hemolysis |
|  | Aggregates regulate apoptosis in cancer patients |
|  | Atherosclerosis |
|  | Malaria |
|  | Infections |
|  | Auto-immune disorders |
|  | Toxic reactions |
|  | Internal bleedings |
| Prion Protein | Creutzfeld-Jacob disease (CJD) |
|  | New variant CJD |
|  | Bovine spongiform encephalopathy (BSE) |
|  | Gerstmann-Straussler-Schheinker disease |
|  | Fatal familial insomnia |
|  | Kuru |
| β-amyloid | Alzheimer's disease |
|  | Down's Syndrome |
|  | Familial Alzheimer's |

TABLE 1-continued

Conformational diseases. See Carrel and Lomas (1997) Lancet 350: 134-138; Carrell and Gooptu (1998) (1998) Curr. Op. Struc. Biol. 8: 799-809; Soto (2001) FEBS letters 498: 204-207; Jaikaran and Clark (2001); Ursini et al. (2002) Trends Mol. Med. 8: 370-374; Kannan et al. (1988) J. Biol. Chem. 263: 13766-13773; Schluter and Drenckhahn (1986) PNAS 83: 6137-6141; Gerner et al. (2002); Davis et al. (2002) Lancet 359: 2242-2247; Fernandez et al. (2001) Atherosclerosis 158, 103, 111 (atherosclerosis); Papalexis et al. (2001) Mol. Biochem. Parasitology 115: 77-86; Esievo et al. (1984) Veterinary Parasitology 15: 181-185; Igoe et al. (2002) Clin. Microb. Newsletter 24: 69-70; Kreidl et al. (2002) J. Am. Coll. Surgeons 194: 387; Beckers (2001) Netherlands J.. Med 58: 207-207 (autoimmune diseases); Ismeno et al. (1999) Int'l J. Cardiology 69: 179-183; Klibansky et al. (1966) Toxicon 3: 213-216; Siebert et al. (2003) Toxicon 41: 831-839; Szabo et al. (2002) Thrombosis Research 107: 357-363; Kaioumova et al. (2001) Chemosphere 43: 801-805.

| Protein | Disease |
| --- | --- |
| α-Synuclein | Parkinson's disease, Lewy bodies |
| Tau protein | Frontotemporal dementia, Pick bodies |
| Serpins | $\alpha_1$-antitrypsin deficiency |
|  | cirrhosis |
|  | emphysema |
|  | Antithrombin deficiency |
|  | thrombosis |
|  | $C_1$-inhibitor deficiency |
|  | angioedema |
| Neuroserpin | Neurodegenerative disease, Collins bodies |
| Glutamate repeats | Inherited neurodegenerative disorders |
|  | Huntington's disease |
| Amylin | Diabetes type II |
| SOD | Amyotrophic lateral sclerosis |
| ApoB | Atherosclerosis |
| CFTR protein | Cystic fibrosis |
| Immunoglobulin | Systemic amyloid light chain amyloidosis |
| Amyloid light chain | Nodular amyloidosis |
| Serum amyloid A | Reactive systemic amyloid A amyloidoses |
|  | Chronic inflammatory disease |
| Transthyretin | Senile systemic amyloidosis |
|  | Familial amyloid neuropathy |
|  | Familial cardiac amyloid |
| $\beta_2$-microglobulin | Hemodialysis amyloidosis |
|  | Prostatic amyloid |
| Apoliproprotein AI | Familial amyloid polyneuropathy |
|  | Familial visceral amyloid |
| Cystatin C | Hereditary (Icelandic) cerebral angiopathy |
| Lysozyme | Familial visceral amyloidosis |

TABLE 2

Congophilic disorders. See Kelly (1996) Curr. Opin. Struct. Biol. 6: 11-17.

| Disorder Acronym | Disorder | Protein Involved |
| --- | --- | --- |
| CJD | Spongiform encepalopathies | Prion protein fragments |
| APP | Alzheimer | Beta protein fragment 1-40/43 |
| HRA | Hemodialysis-Related Amyloidosis | Beta-2 microglobin* |
| PSA | Primary Systematic Amyloidosis | Immunoglobulin light chain and fragments |
| SAA 1 | Secondary Systematic Amyloidosis | Serum amyloid A 78 residue fragment |
| FAP I** | Familial Amyloid Polyneuropathy I | Transthyretin fragments, 50+ alleles |
| FAP III | Familial Amyloid Polyneuropathy III | Apolipoprotein A-1 fragments |
| CAA | Cerebral Amyloid Angiopathy | Cystatin A minus 10 residues |
| FHSA | Finnish Hereditary Systemic Amyloidosis | Gelsolin 71 residue |

TABLE 2-continued

Congophilic disorders. See Kelly (1996) Curr. Opin. Struct. Biol. 6: 11-17.

| Disorder Acronym | Disorder | Protein Involved |
|---|---|---|
| IAPP | Type II Diabetes | Islet amyloid polypeptide fragment |
| ILA | Injection-Localized Amyloidosis | Insulin |
| CAL | Medullary Thyroid Carcinoma | Calcitonin fragments |
| ANF | Atrial Amyloidosis | Atrial natriuretic factor |
| NNSA | Non-Neuropathic Systemic Amylodosis | Lysozyme and fragments |
| HRA | Hereditary Renal Amyloidosis | Fibrinogen fragments |

*Homologous to immunoglobin, thus a predicted paralogous disease.
**Also called senile systemic amyloidosis, prealbumin is synonymous with transthyretin. See mad-cow.org/congo.html. (the prefix "www" is required).

Immunohistochemical assays have been developed for the proteins listed in Tables 1 and 2. See, e.g., Hardt et al. (2000) *J. Comp. Path.* 122:43-53 (antibodies for the detection of the prion protein, PrP). However, many of these proteins are only abundant in the late stages of the disease and may be undetectable utilizing standard assay techniques. Thus, in one embodiment, the methods of the present invention may be combined with an immunochemical assay for the protein or proteins selected from Tables 1 and 2. These proteins, or their functional derivatives, may be detectably labeled with any appropriate marker such as a radioisotope, an enzyme, a fluorescent label, a paramagnetic label, or a free radical linked to an antibody capable of binding these proteins.

Methods of making and detecting such detectably labeled antibodies or their functional derivatives are well known to those of ordinary skill in the art, and are described in more detail below. See, for example, Klein (1982) *Immunology: The Science of Self-Nonself Discrimination* (John Wiley & Sons, New York 1982); Kennett et al. (1980) *Monoclonal Antibodies and Hybridomas: A New Dimension in Biological Analyses*, (Plenum Press, New York; Campbell (1984) *Monoclonal Antibody Technology, Laboratory Techniques in Biochemistry and Molecular Biology*, ed. Davis et al. 3d ed.; Harper & Row, Philadelphia. Methods for the generation of polyclonal antibodies are known, as are techniques of the generation of monoclonal antibodies. See, e.g., Kohler and Milstein (1975) *Nature* 256:495-497.

Assay techniques useful in the present invention include, but are not limited to, assays comprising incubating a biological sample from a subject from a subject suspected of having such a condition in the presence of a detectably labeled binding molecule (e.g., antibody) capable of identifying the relevant protein, and detecting the binding molecule which is bound in a sample. See, e.g., Work et al. (1978) *Laboratory Techniques and Biochemistry in Molecular Biology* (North Holland Publishing Company, NY.

Alternatively, the proteins contained in a particular sample of proteons can be identified by screening against a panel of phage antibodies in which the displayed peptide is a domain of the antibody molecule that includes the site that binds antigen. Phage-antibody libraries can be constructed including billions of clones, displaying billions of antibodies with different antigen specificities. For a review of this technique, see Petrenko and Vodyanoy (2003) *J. Micro. Meth.* 53:253-262.

The presence of proteons themselves can be detected and quantitated by dark field microscopy. Under high-resolution dark-field microscopy proteons are visualized as bright spherical shapes. Techniques for dark-field microscopy are known in the art. See, e.g., Bradbury and Bracegirdle (1998), *Introduction to Light Microscopy (Microscopy Handbooks, No* 42), 2d ed.; (Springer Verlag). In particular, proteons are small, ball-like bodies of different sizes, estimated in the range of 50-250 nm. By contrast, healthy erythrocytes appear as bright void circles of about 7 microns diameter in the dark-field view, whereas neutrophils are roughly 7-15 microns. When a blood sample comes aged, the morphology and number of the proteons change, with some estimated to be 500 nm in diameter. Proteons are found in fresh blood of species including human, bovine, horse, pig, cat, dog, fish, rabbit, and rat blood.

Dark-field microscopy of proteons can be confirmed by transmission electron microscopy (TEM) and scanning electron microscopy (SEM) methodology. Techniques for electron microscopy are known in the art. See, e.g., Slayter and Slayter (1992) *Light and Electron Microscopy*, (Cambridge University Press).

Proteons can be isolated from blood or plasma, i.e., the supernatant produced by centrifuging a biological material. In one embodiment, proteons can be formed by incubating plasma at 37° C. under sterile conditions over a thirteen day period. At the end of this period, the numbers of proteons observed under dark-field light microscopy are greatly increased.

In another embodiment, large numbers of proteons are produced by subjecting plasma to 120° C. at 20 psi for two hours. The visible number of proteons is amplified by subjecting plasma to single step of elevated temperature.

Efficiency of proteon production is enhanced by taking a small proton of an amplified sample, adding it to an untreated sample and heating the untreated sample. These steps can be repeated a number of times, each iteration yielding an increased quantity of proteons. Accordingly, by dividing the sample into a number of subsamples, subjecting the first subsample into the second subsample and carrying out the heating step, a greater concentration of proteons can be produced from the second subsample than was produced form the first subsample. These seeding steps can be repeated multiple times until, after several iterations, the concentration of proteons produced per volume of sample eventually plateaus.

Typically, the first two cycles result in a small but significant increase of proteon population, wherein the third cycle brings about a dramatic increase in the number of proteons. Generally, the next three cycles result in saturation of the proteon population.

In one embodiment, a test sample containing a small amount of misfolded proteins is subjected to a single heating step. The amplified proteons are quantitated by dark-field microscopy and verified by immunofluorescent techniques to detect the misfolded protein.

In another embodiment, a small amount of seeds such as the PNCs described above can be added to a test sample to increase the sensitivity of the single step methods. Roughly $5 \times 10^{13}$ PNC/ml are produced by initial filtration of plasma through a 5 kD filter. This concentration then can be increased by a factor of roughly 100 by evaporation. Thus, in one aspect, addition of 5 ml of $5 \times 10^{13}$ PNC/ml to a 1 ml sample increases the concentration of PNC in a sample by $2.5 \times 10^{11}$ PNC/ml. This concentration is increased by a factor of 100 if pre-concentrated PNC are added. If the initial concentration of PNC varies from $10^8$ to $10^{11}$ PNC/ml, the sensitivity can be increased by a factor of between 250 to 250,000.

In another embodiment, the first step amplification described above is carried out, then a small portion of amplified sample is introduced into the untreated sample and subjected to heat again. Then, the small portion of the second amplified sample is added to the third untreated sample, heated and so on. The number of cycles depends on the initial concentration of misfolded proteins. Suitable numbers of cycles include 1, 2, 3, 4, 5, 6, 7, 8, 9, 10, 15, 20, 25, or more.

In one embodiment, the detection and identification can be done as a single-step method. Apparatus for subjecting a sample to heat and/or pressure are recognized in the art and include without limitation, PCR thermocyclers, autocalves, etc.

As will be recognized by one of skill in the art, both the single- and multiple-step methods can be manipulated by varying the temperature, pressure, or temporal parameters. Suitable temperatures include 37, 40, 45, 50, 55, 60, 65, 70, 75, 80, 85, 90, 95, 100, 105, 110, 115, or 120° C. Suitable pressures include ambient pressure, as well as 14, 15, 16, 17, 18, 19, 20, 21, 22, 23, 24, or 25 psi. Suitable times of treatment include 1, 5, 10, 15, 20, 25, 30, 35, 40, 45, 50, 55, 60, 65, 70, 75, 80, 85, 90, 95, 100, 105, 110, 115, and 120 minutes.

In another embodiment, these methods can be utilized to clear misfolded proteins from a biological sample such as blood. Because low temperatures can be utilized with long time periods, this can be accomplished without damaging the biological sample.

In another embodiment, these methods can detect misfolded proteins involved in congophilic disorders. See Kelly (1996) *Curr. Op. Struc. Biol.*, 6:11-17; Kelly (1996) 8:101-106. For instance, there is a demonstrated structural homology between prion and hemoglobin proteins. Korth et al. (1997) *Nature* 390:74-77. There is evidence that prions are present in lymphoid organs and blood. See, e.g., Brown et al. (2001) *J. Lab. Clin. Med.* 137:5-13; Aguzzi (2000) *Lab. Clin. Med.* 137:5-13; Aguzzi (2001) *Nature Medicine* 7:289-290; Wadsworth et al. (2001) *Lancet* 358:171-180. Accordingly, the methods of the present invention can be utilized for amplification of a congophilic protein, thus allowing early detection of disorders related to these proteins.

PNC of roughly 1-2 nm and containing about 40-300 atoms play an important role in capturing hemoglobin released into blood plasma. While released hemoglobin can be collected by PNCs. Roughly $7 \times 10^{13}$ PNC are present in each milliliter of human blood, while only 0.003% of the whole pool of PNC is normally linked to proteins and made into proteons. However, a proteon of medium size of 160 nm can collect about 100,000 protein molecules of similar size to hemoglobin. Thus, the strong protein scavenging properties of metal nanoparticles allow them to collect proteins include misfolded hemoglobin (Kristiansen et al. (2001) *Nature* 409:198).

Thus, in another embodiment, the present methods can be utilized for amplification of proteins involved in intravascular hemolysis and resulting in aggregation of hemoglobin, including, without limitation, sickle cell anemia, atherosclerosis, malaria, infections and their complications, auto-immune disorders, internal bleedings and intravascular hemolysis due to internal prosthetic devices, and toxic reactions. See Kannan et al. (1988) *J. Biol. Chem.* 263:13766-13773; Schluter and Drenckhahn (1986) *PNAS* 83:6137-6141 (sickle cell); Fernandez et al. (2001) *Antherosclerosis* 158, 103-111 (atherosclerosis); Papalexis et al. (2001) *Mol. Biochem. Parasitology* 115:77-86; Esievo et al. (1984) *Veterinary Parasitology* 15:181-185; Igoe et al. (2002) *Clin. Microb. Newsletter* 24:69-70; Kreidl et al. (2002) *J. Am. Coll. Surgeons* 194:387; Beckers (2001) *Netherlands J. Med:*58:204-207 (autoimmune diseases); Ismeno et al. (1999) *Int'l J. Cardiology* 69:179-183; Klibansky et al. (1966) *Toxicon* 3:213-216; Seibert et al. (2003) *Toxicon* 41:831-839; Szabo et al. (2002) *Thrombosis Research* 107:357-363; Kaioumova et al. (2001) *Chemosphere* 43:801-805.

Using standard techniques, samples for single-step or cyclic amplification can be prepared from homogenates of small tissue fragments, or from biological fluids such as blood, cerebrospinal, lymph, etc. Techniques for the preparation of tissue homogenates and biological fluids from such sources are known. See Sambrook et al. (1989) *Molecular Cloning—A Laboratory Manual*, Vols. 1-3 (2d ed; Cold Spring Harbour Laboratory Press, Plainview, N.Y.); and Ausubel et al., eds. (1994) *Current Protocols in Molecular Biology*, (Green Publishing Associates, Inc. and John Wiley & Sons, Inc.).

PNCs can be produced from plasma by filtration through an ultrafiltration membrane. In one embodiment, plasma is filtered consecutively through a 30 kD and a 5 kD CENTRICON™ filter (Millipore Corp.) before heat treatment. The centrifuge filtration is carried out using an initial volume of 80 ml centrifuged at 3,500 g for 20 minutes, 20° C.

Filtration of plasma before heat treatment abolished proteon formation in the retentate. However, recombination of the recombination of the fractions results in the resumption of proteon formation, and the number of proteons formed is dependent upon the amount of filtrate added back to the retentate. Thus, the PNCs are present in the filtrate.

Absorption spectra of the filtrate reveals the presence of metals, including copper, zinc, and iron, indicating that PNCs comprise metals. The filtrate was precipitated with 1.2 mM $MsSO_4$ and TEM studies were carried out. Such procedures are known in the art. See, e.g., Shindo and Oikawa, *Analytical Electron Microscopy for Materials Science*, Springer-Verlag (2002). It was found that the precipitated extract contained crystalline metallic nanoparticles of roughly 1-2 nm diameter. Selected area diffraction patterns were consistent with the presence of face centered cubic (FCC) or body centered cubic (BCC) metals or solid-solution alloys such as FCC copper and BCC iron.

For a review of metal clusters, see Aiken and Finke (1998) *J. Mol. Cat. A:Chem.* 145:1-44; Gonzalez-Moraga (1993) *Cluster Chemistry* (Springer-Verlag, New York, N.Y.). High symmetry is one of the main characteristics of metal clusters (Gonzalez-Moraga (1993) (*Supra*). In addition, metal clusters bind proteins. See Broun et al. (2002) *J. Mol. Biol.* 321: 341-353; Lui and Xu (2002) *J. Inorganic Biochem.* 88:77-86. This in one embodiment, the PNCs of the invention are characterized by small size, a few nm or smaller. Additionally, the PNCs are present in large quantities, about $10^{12}$-$10^{13}$ PNC/$cm^3$ of blood or tissue, are abundant, present binding sites and strong affinity to proteins, exhibit variability to bind different proteins, and resist extreme physical and biochemical conditions.

To test the effects of PNCs isolated from the filtrate upon living cells various amounts of PNCs obtained by ultrafiltration and sterilized by autoclaving were incubated for four hours with various animal cells in tissue culture. Significant effects upon cell viability were observed. For instance, rat and mouse glioma cells demonstrated marked signs of cell death, as assessed both microscopically and by MTT assay. Accordingly, the PNCs of the invention comprise a novel reagent for use in inducing apoptosis, as well as a process for its production. In one embodiment, aliquots from 1 to 40 µl containing about $1 \times 10^{12}$ to $4 \times 10^{13}$ PNCs were added to 100 µl wells of 96-well ELISA plate. Such compounds and processes are great for usefulness to those of skill in the art. See, e.g., U.S. Pat. No. 5,344,926 to Murakata et al., titled "Process for producing staurosporine fermentation process"; and U.S. Pat.

No. 6,518,032 to Fritz et al., titled "Rapid methods for identifying modifiers of cellular apoptosis activity."

This invention is further illustrated by the following examples that should not be construed as limiting.

EXPERIMENTAL

Example 1

Production of Proteons from Blood and Analysis by Microscopy

A 30 µl sample of freshly drawn full blood from a healthy human male was obtained and diluted in 1000 µl of purified water (17 MOhm) in a 1.5-ml plastic vial, and centrifuged at 2200 g (6000 rpm) to obtain plasma. An additional aliquot of the blood was taken and prepared for optical dark-field microscopy. The plasma was transferred to a 4-ml glass vial with a plastic cap and a Teflon liner. An aliquot of plasma was again retained for dark-field microscopy. The vial and contents were subjected to heating at a temperature of 120° C. and 20 psi of pressure for two hours. An aliquot of the heat-treated plasma was prepared for dark-field microscopy.

Each aliquot retained for microscopy was analyzed by dark-field microscopy using an OLYMPUS™ microscope fitted with a 100 W mercury lamp, a polarizer, and a Naessens dark-field condenser (COSE Corp., Canada).

After analysis, the fresh full blood sample was found to contain approximately $3 \times 10^8$ proteons/ml, whereas the diluted sample contained roughly $9 \times 10^6$ proteons/ml. The treated sample contained an estimated $3 \times 10^{11}$ proteons/ml, a five-order of magnitude increase. Adjusted for the initial dilution of the blood sample, each milliliter of blood yielded roughly $1 \times 10^{13}$ proteons. Thus, within two hours, the number of proteons increased by approximately 5 orders of magnitude. Assuming exponential growth, then the number of proteons (N) at any given moment of time (t) can be described by the equation:

$$N = N_0 e^{bt} \qquad (1)$$

where $N_0$ is the initial number of particles, and b is the growth coefficient. If N, $N_0$, and t are substituted with the experimental values found in the above experiment, one can estimate that the growth coefficient (b) for this case is equal to 5.2 1/hour, and the proteon population is doubled every 8 minutes.

As a control, a suspension of phospholipids and cholesterol was subjected to the same protocol used for the blood sample. However, no structures resembling proteons were observed under dark-field microscopy.

Electron microscopy analysis was also carried out on samples obtained before and after heat treatment. Transmission electron microscope (TEM) images obtained from pre- and post-heat-treatment samples reveal small proteons appearing as dark discs with a rough fibrous appearance. An analysis of the TEM images revealed the size distribution of this characteristic small proteon to reach a maximum about 150 nm.

Another characteristic form of proteon was observed, a coconut-shaped particle of about 1-5 microns with a structure resembling one or more nuclei and a cell-like appearance. The nuclei look very similar to the small proteons described above. A cross-sectional view of a larger proteon reveals a very distinctive external membrane-like structure. This membrane-like structure, however, looks very different from the bacterial wall or the mammalian cell membrane, appearing as a curly fibrous shell of 10-12 nm thick. Some fiber-like structures and a few nuclei are visible inside the proteon. Images obtained by scanning electron microscopy (SEM) confirm the presence of both small and large characteristic proteons.

Example 2

Chemical Composition of Proteons

Energy Dispersive Spectroscopy Analysis

The chemical composition was determined by energy dispersive X-ray spectroscopy using a JEOL JSM-840 SEM system using standard procedures for identifying and quantifying elemental composition. Such procedures are known in the art. See, e.g., Shindo and Oikawa (2002) *Analytical Electron Microscopy for Materials Science* (Springer-Verlag).

A sample of proteons suspended in distilled water was deposited on the aluminum SEM mount and dried in a vacuum for 24 hours. The X-ray spectra were obtained with an electron beam size of 200 nm at 80 kV for 90 s. Spectra revealed that the proteons were composed of carbon, oxygen, nitrogen, and sulfur, and the presence of potassium, sodium, chloride, silicon, and copper was also detected. The presence of carbon, nitrogen, and sulfur was confirmed by analytical chemical analysis (Leco Corporation, Michigan, U.S.A.). Notably phosphorus, a necessary element of DNA, was never detected in the proteon samples. On the other hand, all the elements needed for amino acids and proteins are available.

Amino Acid Composition

Free amino acid composition of samples before and after heat and high pressure treatment were determined (LPSA, University of Arizona, Tucson, Ariz.). See Table 3.

TABLE 3

| | Amino acid composition (pmol/50 µl) | | |
|---|---|---|---|
| No | Amino Acid | Control* | Proteons |
| 1 | O-Phosphoserine | 98.730 | 39.878 |
| 2 | Taurine | 191.790 | 227.739 |
| 3 | O-Phosphoethanolamine | 17.980 | 15.318 |
| 4 | Urea | 220.811 | 62.573 |
| 5 | Aspartic Acid | 137.212 | 123.086 |
| 6 | Threonine | 365.225 | 214.981 |
| 7 | Serine | 385.160 | 314.039 |
| 8 | Asparagine | — | 95.908 |
| 9 | Glutamic Acid | 483.645 | 229.149 |
| 10 | Glutamine | 287.073 | 3.920 |
| 11 | Glycine | 985.419 | 922.430 |
| 12 | Alanine | 443.165 | 448.792 |
| 13 | Citralline | 81.803 | — |
| 14 | Valine | 188.720 | 236.126 |
| 15 | Cystine | 4.799 | 6.367 |
| 16 | Methionine | — | 77.583 |
| 17 | L-Cystathio-nine | 12.301 | 16.417 |
| 18 | Isoleucine | 82.836 | 76.302 |
| 19 | Leucine | 121.941 | 139.060 |
| 20 | Tyrosine | 68.636 | 75.682 |
| 21 | Phenylalanine | 104.921 | 79.904 |
| 22 | y-Amino-butiric Acid | — | 108.022 |
| 23 | Etanolamine | 36.578 | 35.605 |
| 24 | L-Ornithine | 53.341 | 23.004 |
| 25 | Lysine | 226.033 | 208.597 |
| 26 | Histidine | 75.954 | 103.043 |
| 27 | Agrinine | 273.221 | 166.512 |

*Preheat and high-pressure treatment plasma.

Protein Concentration

The quantitative analysis of proteins in the proteon samples was carried out by two different protein assays obtained from Bio-Rad Laboratories and Sigma Chemical Company according to the manufacturers' protocols. Samples of blood as described in the Example 1 were exposed to different temperatures and pressures. Results of the experiments are shown in Table 4.

TABLE 4

Protein concentration in proteon samples

| Sample, Condition | BIO-RAD, Protein concentration | SIGMA, Protein concentration, µg/ml |
|---|---|---|
| Plasma, control, 25° C. | 0.67 ± 0.05 | 0.85 ± 0.2 |
| Plasma, 56° C., normal pressure, 10 min | 0.72 ± 0.04 | 0.98 ± 0.02 |
| Plasma, 80° C., normal pressure, 10 min | 0.68 ± 0.04 | 1.0 ± 0.2 |
| Proteons, 120° C., 20 psi, 2 hours | 0.71 ± 0.04 | 1.7 ± 0.2 |

Gel electrophoresis of plasma and two major protein components of plasma, albumin and hemoglobin, treated with 120° C. heat and 20 psi pressure produce obvious bands of 66,200 D and 14,400 D. Thee are shared with albumin and hemoglobin, respectively. After the treatment, the albumin has two weak bands of 14,400 D. These are shared with albumin and hemoglobin, respectively. After the treatment, the albumin has two weak bands of 14,400 D and ~8,000 D, which coincide with the same bands of proteons. The treated hemoglobin conserved only the 8,000 D band. Proteons filtered through a 100 kD filter conserved the 14,400 and ~8,000 bands, while proteons washed from the filter contain practically all bands of plain proteons, indicating that misfolded albumin and hemoglobin may be present in proteons. The confirmation of this fact may be obtained from the immuno-blotting analysis.

Proteons from rabbit blood were disassembled by sodium dodecyl sulfate (SDS), a negatively charged detergent. The fragments of proteins were electrophoresed down and made distinctive bands in the polyacrylamide gel. The proteins were identified by N-terminal amino acid sequencing, yielding the partial sequence VLSPA (D/E)(E/K)TN(A/I) (SEQ ID NO:1) that shows 100% homology with the rabbit alpha chain of hemoglobin. Amino acid analysis showed that proteons are enriched by hydrophilic negatively charged amino acids, glutamic and aspartic acids. Proteons stained with congo-red show an apple-green birefringence with polarizing light indicating the anisotropic alignment of the dye molecules.

Congo-red staining is indicative of a common structural feature shared by many amyloids. Specifically, they are stabilized in part by anti-parallel beta sheet extension from one monomer to another. It is believed that they dye binds to inter-monomer clefts between anti-parallel beta edge strands. See Kelly (1996) Curr. Op. Struc. Biol. 6:11-17; Kelly (1996) Curr. Op. Struc. Biol. 8:101-106. One protein belonging to the congophilic family is the prion protein associated with the prion diseases. A structural homology between prion and hemoglobin proteins has been demonstrated (Korth et al. (1997) Nature 390:74-77). In particular, two prion PrP(121-231) molecules could be superimposed with two β subunits of the crystal lattice of sickle cell hemoglobin 1HBS. The superposition included the backbone atoms of residues 145-154, 179-189, and 201-217 of the helices 1, 2, and 3 of PrP(121-231) and of residue 5-14, 106-116, and 125-141 of the helices 1, 6, and 7 of hemoglobin S.

Absence of DNA in Proteons

An aliquot of blood pre- and post-treatment (see Example 1) was purified using the DNeasy™ genomic DNA isolation tissue kit (Qiagen) according to the manufacturer's standard protocols for animal blood and bacteria. After final elution, samples were loaded on 1% agraose gel. DNA bands were visualized with ethidium bromide. DNA was detected in pre-treatment sample and undetected in the post-treatment sample.

Similar results were obtained using a HIGH PURE™ PCR template preparation kit (Roche Corp.) for isolation of Nucleic Acids followed by fluorometric quantitation of double-stranded DNA using the PICOGREEN® dsDNA quantitation reagent (Molecular Probes Inc.) and a TEACAN SPECTRAFLUOR PLUS™ fluorescence and absorbance reader equipped with DELTASOFT™ software for detecting fluorescence (excitation at 485 nm and emission at 535 nm). See Table 4.

TABLE 5

Flourometric quantitation of DNA in blood and proteons.

| Sample | DNA concentration, µg/ml |
|---|---|
| Blood | 45.1 |
| Blood after dilution and centrifugation | 3.0 |
| Proteons, freshly prepared | 0.033 |
| Proteons, 3 months old | <0.001 |

Example 3

Controlled Growth of Proteons

Two identical sets of samples were prepared for this experiment, in which the growth of proteons incubated at 37° C. in an atmosphere of ambient air was compared with the growth of proteons incubated in an atmosphere of 5% $CO_2$. Each set included the following numbered groups:

Group 1. Three ml of freshly prepared proteons (as described in Example 1).

Group 2. Three ml of plasma after dilution and centrifugation (as described in Example 1).

Group 3. Ten µl of freshly prepared proteons added to 3 ml of D6429 tissue culture media (Sigma Inc.) with 10% FBS (HyClone Labs. Inc.).

Group 4. Ten µl of freshly prepared proteons added to 3 ml of D5648 tissue culture media (Sigma Inc.) with 10% FBS (HyClone Labs. Inc.).

Group 5. Ten µl of freshly prepared plasma added to 3 ml of D6429 tissue culture media (Sigma Inc.) with 10% FBS (HyClone Labs. Inc.).

Group 6. Ten µl of freshly prepared plasma added to 3 ml of D5648 tissue culture media (Sigma Inc.) with 10% FBS (HyClone Labs. Inc.).

The experiment was run in duplicate. Uninoculated media were used as a control. Samples were analyzed by dark-field and scanning electron microscopy at the time points of 0, 2, 4, 8, and 13 days.

Optical observation of proteons was performed with an OLYMPUS™ microscope fitted with a 100-W mercury lamp illumination source, a polarizer, a Naessens dark-field condenser (COSE Corp., Canada) and a 100× objective (oil, NA 1.4). The dark-field images were directed to a DEI-470T™ microscope video camera (Optronics Engineering, CA) utilizing the methods described in Vodyanoy et al. (1994) Langmuir 10:1354-1357. A direct count of proteons was used to determine their concentrations in liquid samples, and IMAGE PRO™ software (Creative Software, Inc.) was used to quantify the number of proteons.

The number of proteons incubated at 37° C. in an atmosphere of ambient air (Group 1) measured by dark-field microscope did not change significantly ($p<0.01$) during 13 days (FIG. 2A, line 1). The plasma at the same conditions (Group 2) showed a very small increase in population of proteons within 8 days of incubation, but the number increased dramatically and reached the number of proteons in group 1 after 13 days of incubation (FIG. 2A, line 2). Proteons and plasma in tissue culture media (Group 3 and 4, respectively) exhibited the same growth curves and reached the same number of proteons after 13 days of incubation (FIG. 2B). The culture media alone incubated at the same conditions showed no proteons (FIG. 2B, bottom line). No significant ($p<0.01$) effect of $CO_2$ was observed.

Example 4

Reversibility of Construction and Deconstruction of Proteons In Vitro

Plasma was prepared as described in Example 1. The samples of plasma were combined with the guanidine hydrochloride or urea to a final concentration of 0, 0.01, 0.1, 1, 4, and 8 M, respectively. These chaotropic compounds are known to unfold and denature proteins.

Samples were subjected to heat of 120° C. and pressure of 20 psi. In the samples to which no chaotropic compounds were added, the numbers of proteons observed by dark-field microscopy was normally high. The number of proteons decreased as the concentration of chaotropic compounds was increased (FIG. 2C).

Samples of proteons grown at the suppressive presence of 8 M urea were subjected to dialysis using a Pierce Chem. Co. SLIDE-A-LYSER™ 10K dialysis cassette (20 h, 5 L, 20° C.) according to the manufacturer's instructions. The number of proteons found by dark-field microscope increased significantly. Samples of plasma treated with 120° C. heat d 20 psi pressure and urea at concentrations of 0.01-8 M were taken. Polyacrylamide gel electrophoresis was carried out on each sample with a 4-20% Tris-HCl READY™ precast gel (Bio-Rad Labs. Inc.) according to the manufacturer's protocol. The control (proteons without chaotropic compounds) showed two characteristic bands of 14,400 and about 8,000 D. The experimental samples (proteons in the presence of a chaotropic compound) displayed a diffuse distribution of proteins or fragments of proteins with no sharp bands of proteins of the high molecular mass range. As the concentration of urea increased, the intensity of the diffusion staining decreased, and almost fully disappeared at the 8 M concentration of urea. The proton sample displays a 14,400 D band that coincides with a similar band found in plasma. When guanidine hydrochloride or urea was added to proteons produced without the chaotropic compounds, heat of 120° C. and pressure of 20 psi resulted also in a great reduction of number of proteons visible by dark-field microscopy. Dialysis of these samples restored the population of the proteons. Gel electrophoresis of proteons and plasma treated with 120° C. heat and 20 psi pressure at the presence of urea, and then dialyzed, reveals two bands of 14,400 and about 8,000 D in all samples, including those before and after dialysis.

Example 5

Effect of Ultrafiltration on Proteon Formation

PNCs were removed from blood plasma by filtering the plasma through 5 kD CENTRICON™ filters (Millipore Corp.) according to the manufacturer's protocol. The protein level in the retentate was quantitated and compared to that of unfiltered plasma Assay kits were obtained from Bio-Rad Laboratories, and quantitative studies were carried out according to the manufacturer's instructions. The amount of protein in the filtered plasma was the same as that measured in the non-filtered sample. No protein was detected in the filtrate. After filtration, proteons could not be produced until the filtered fraction was returned to the plasma. The number of proteons was dependent on the amount of filtrate returned to the retentate. Addition of 10 mM of the chelating agent, ethylene diamine tetra acetate (EDTA), known to form strong complexes with metals, also prevented the formation of proteon. Adsorption spectra of the filtrate, determined by energy dispersive x-ray spectroscopy (EDS) and inductively coupled plasma-atomic emission spectrometry (GTW Analytical Services, TN), revealed the presence of metals, including Cu, Zn, and Fe.

Example 6

Analysis of PNCs

To characterize the nature of the PNC nanoparticles, transmission electron microscopy (TEM) was utilized. Transmission electron microscopy (TEM) was utilized. Transmission electron microscopy (TEM) was performed using a JEM 2010™ instrument (JEOL Ltd.), operated at 200 kV. Bright-field (BF) imaging was used to provide an overview of the microstructure of the sample. Features of interest were characterized by selected area diffraction (SAD) and nanobeam diffraction (NBD, with the latter set up to produce a narrow (<50 nm diameter), yet near-parallel beam, so that SAD-like patterns were produced. Dark-field (DF) imaging was employed to determine which microstructural features gave rise to the diffraction maxima. The composition of microstructural features was determined (qualitatively) by means of energy dispersive x-ray spectroscopy (EDS). This work employed an ultra-thin window (UTW) detector (Oxford Instruments plc), attached to the JEM 2010™ instrument, together with an ISIS™ analyzer (Oxford Instruments plc).

Scanning electron micrographs were obtained using a JSM-840™ SEM system (JEOL Ltd.). Plasma from rabbit blood was filtered consecutively through a 30 kD and a 5 kD CENTRICON™ filter (Millipore Corp.) before heat treatment. PNCs were precipitated from the filtrate by 1.2 mM $MgSO_4$ at pH 11.3 and transferred onto 400 mesh Ni/carbon grids (Electron Microscopy Sciences Co.). Proteon samples for TEM were fixed with 3% gluteraldehyde, dehydrated with ethanol, and embedded in DURCUPAN™ ASM resin (Fluka Co.).

The bulk of the blood precipitate from rabbit plasma was amorphous. However, this extract was found to contain crystalline metallic nanoparticles, with diameters of around 1-2 nm and above. SAD patterns originating from different regions of the samples were consistent with the presence of both face centered cubic (FCC) and body centered cubic (BCC) metals (or possibly solid-solution alloys), with lattice parameters ($a_0$) of approximately 360 and 290 pm respectively. These combinations of Bravais lattice and $a_0$ are close to those of FCC copper ($a_0$=361.50 pm (International Centre Diffraction Data (2001), Powder Diffraction File, ICCD, Newtown Square, Pa.)) and BCC a-iron ("ferrite", $a_0$=286.64 pm (International Centre Diffraction Data (2001)), Powder Diffraction File, ICCD, Newtown Square, Pa.)), respectively. Furthermore, both copper and iron were encountered in EDS spectra acquired from the regions containing the nanoparticles. Centered DF imaging demonstrated that the diffraction maxima in these patterns originated from the nanoparticles. When viewed in BF, the metallic nanoparticles were very difficult to distinguish from the amorphous background in most regions of the samples. Hence, such particles could easily have been overlooked in the BF imaging techniques used conventionally for biological electron microscopy.

The observed crystallography of non-clumped nanoparticles was that of metallic iron and copper, rather than of salts of these metals. Furthermore, the diffraction patterns encountered in this work were not produced by an organometallic structure. The production of even nanometer-sized metallic particles implies assembly of a significant number of metal atoms. For example, a 1 nm diameter Cu particle has the same volume as around 10 Cu, or 20 α-Fe, unit cells. FCC metals have 4 atoms per unit cell and BCC metals 2 atoms per cell, indicating a particle containing around 40 atoms in both cases (similarly, a 3 nm diameter particle would contain over 1,000 atoms).

Individual metallic nanoparticles had a random crystallographic orientation. Thus, in cases where particles had become clumped (in some cases, this appeared to involve flocculation, in others some of the particles had sintered together), a polycrystalline aggregate was produced. In contrast, within a number of relatively large (around 10 nm diameter or above) clumps of particles, significant (~5-10 nm wide) regions were encountered with a constant crystallographic orientation. However, none of the clumps was a true single crystal. Some of these relatively large clumps contained a number of, as yet unidentified, second phases in addition to α-Fe and Cu.

Both Cu and Fe form stable oxides (for example the Gibbs free energy of formation of even the relatively low stability CuO phase is around −127 kJ mol$^{-1}$ at 300 K). See Brandes and Brook (1992) *Smithells Metals Reference Book* (7$^{th}$ ed., Butterworth-Heinenmann, Oxford, UK). Furthermore, the initial stages of oxidation of these metals are rapid, even at room temperature. For example, logarithmic oxidation of initially bare iron, at an oxygen partial pressure of only 10 mPa, results in the growth of around 2 nm of oxide, after less than 20 minutes at 300 K. See Kruger, J. and Yolken (1964), cited by Lawless. (1974) *Rep. Prog. Phys.* 37(2):231-316. The presence of non-noble metallic nanoparticles implies that the surrounding organic matrix has either impeded oxygen access to the metallic particles and/or has a significant reducing effect.

Many of the nanoparticles survived the coarsening. The surface energy of the particles provides a driving force for larger particles to cannibalize smaller particles (the surface area to volume ratio for a 1-nm particle is $6 \times 10^9$ m$^{-1}$ and this drops by an order of magnitude for a 10-nm particle). Metallic materials have relatively high solid-vapor interfacial energies ($\gamma_{SM} \ll \gamma_{SV}$, there would remain a significant thermodynamic driving force for coarsening. Given the kinetics of coarsening, if all that were present were the metallic nanoparticles, room-temperature coarsening, if all that were present were the metallic nanoparticles, room-temperature coarsening would occur at a negligible rate (solid-state sintering involves bulk diffusion, interfacial diffusion, free surface diffusion and evaporation and re-condensation, all of which would be very slow for Cu or α-Fe at room temperature). See Ashby (1974), *Acta Metallurgica* 29(2):259-281. Although the presence of the organic liquid matrix raises possibilities for mass transport, it appears that the matrix did not provide a path for rapid transfer of metal atoms since many of the nanoparticles of served in the present work remained extremely fine.

Example 7

In Vitro Effect of PNC on Cultured Cells

The impact of PNCs upon viability of various cultured cells was investigated using tetrazollium salt (MTT) cell proliferation assay. RG2 (mouse brain glioma), F98 (rat brain glioma), Hs683 (human brain glioma), CTX TNA2 (rat transfected astrocyte), H9c2[2-1](rat heart myocardium), 27FR (rat skin fibroblast), and SVGp12 (human brain astroglia) cells were obtained from American Type Culture Collection (ATCC) and maintained as recommended by ATCC. MTT cell proliferation assays are commercially available. See, e.g., MTT cell proliferation assay from ATCC.

Cells were plated in Dubecco's modified Eagle's growth medium (D5648, Sigma Chemical, St. Louis, Mo.)+10% fetal bone serum (FBS) (Hyclone Laboratories, Logan, Utah) in polystyrene 96-well plates at a density $3 \times 10^3$ cells per well. Twenty-four hours after plating, the medium was replaced with DMEM with either staurosporine (100 µl, 1 µM) or PNC (aliquots, 100 µl, $5 \times 10^9$-$3 \times 10^{11}$ PNC/ml). PNCs were isolated from blood obtained from shark, dog, and rabbit using the ultrafiltration protocol described in Example 5. PNCs were autoclaved at 120° C. and 20 psi for 15 minutes before adding to the cell cultures.

After 20 hours of treatment, a 20-µl aliquot of tetrazolium salt (MTT, 5 mg/ml in PBS) was added to the wells, and interaction was allowed to proceed for 4 hours at 37° C. MTT was reduced in metabolically active cells to form purple formazan crystals, which were dissolved by DMSO and quantified by a Bio-Rad™ plate reader. For each cell type, a linear relationship between cell number and absorbance is established, enabling accurate straightforward quantification of changes in proliferation.

In two trials, the effect of PNCs on RG2 cells was studied utilizing the following protocol:

Day 1. Plate out RG2 cells at a density of $3 \times 10^3$ cells/well in D5648+10% FCS and incubate overnight.

Staurosporine (Sigma Inc. Catalog No. S5921), 100 µg, FW 466.5. Dissolve 100 µg staurospine into 214.3 µl DMSO to equal a 1 mM stock solution. Store at −200° C. Dilute stock 1:10 in media to equal 0.1 mM or 100 µM stock.

Dilute as follows:

466.5 gm/1 liter=1 M

100 µg/2.143 ml=100 µM (frozen stock)

use 10 µl/well=1 µM

Day 2. Remove media and add DMEM+1% FCS (100 µl/well). TX put on late afternoon.

Add staurospine, autoclaved shark PNC, and either 10%, 1%, or 0% FCS treatments to cells and incubate overnight.

The results of this study are shown in Tables 6 and 7, below. (Ab. Av.=Absorbance at 550 nm; St. Dv.=Standard Deviation)

TABLE 6

MTT assay on RG2 glioma cells, with 10%, 1% and 0% FCS

Shark Seeds - autoclaved

| Shark 3 | 10% FCS no tx | 10% FCS 20 μl | 10% FCS 10 μl | 10% FCS 1 μl | 1% FCS no tx | 1% FCS 20 μl | 1% FCS 10 μl | 1% FCS 1 μl |
|---|---|---|---|---|---|---|---|---|
|  | 0.533 | 0.298 | 0.404 | 0.482 | 0.731 | 0.408 | 0.496 | 0.707 |
|  | 0.542 | 0.316 | 0.414 | 0.465 | 0.753 | 0.408 | 0.496 | 0.724 |
|  | 0.577 | 0.374 | 0.425 | 0.526 | 0.74 | 0.408 | 0.496 | 0.605 |
|  | 0.516 | 0.369 | 0.409 | 0.467 | 0.633 | 0.408 | 0.496 | 0.633 |
|  | 0.5 | 0.321 | 0.431 | 0.466 | 0.684 | 0.408 | 0.496 | 0.612 |
|  |  | 0.362 | 0.414 |  | 0.693 | 0.408 | 0.496 |  |
|  |  | 0.285 | 0.373 |  | 0.636 | 0.384 | 0.573 |  |
|  |  | 0.298 | 0.393 |  | 0.637 | 0.431 | 0.529 |  |
| Ab. Av. | 0.5336 | 0.32775 | 0.407875 | 0.4812 | 0.688375 | 0.405625 | 0.547875 | 0.6562 |
| St. Dv. | 0.029126 | 0.035568 | 0.018349 | 0.025994 | 0.049494 | 0.023482 | 0.031197 | 0.055432 |

| Shark 3 | Shark Seeds - autoclaved | | | | Stauro- sporine | | | |
|---|---|---|---|---|---|---|---|---|
|  | 0% FCS no tx | 0% FCS 20 μl | 0% FCS 1 μl | 0% FCS 1 μM | 10% FCS water 20 μl | 10% FCS water 20 μl | 1% FCS water 20 μl | 0% FCS water 20 μl |
|  | 0.866 | 0.432 | 0.739 | 0.827 | 0.406 | 0.436 | 0.726 | 0.971 |
|  | 0.891 | 0.432 | 0.739 | 0.895 | 0.411 | 0.462 | 0.701 | 0.74 |
|  | 0.695 | 0.432 | 0.739 | 0.918 | 0.399 | 0.394 | 0.676 | 0.79 |
|  | 0.937 | 0.432 | 0.739 | 0.833 |  |  |  |  |
|  | 0.799 | 0.463 | .0638 | 0.78 |  |  |  |  |
|  | 0.909 | 0.479 | 0.677 |  |  |  |  |  |
|  | 0.928 | 0.452 | 0.577 |  |  |  |  |  |
| Ab. | 0.949 | 0.551 | 0.574 |  |  |  |  |  |
| Av. | 0.87175 | 0.466625 | 0.648625 | 0.8506 | 0.405333 | 0.430667 | 0.701 | 0.833667 |
| St. Dv. | 0.085951 | 0.038049 | 0.059625 | 0.055599 | 0.006028 | 0.034312 | 0.02 | 0.121533 |

TABLE 7

MTT assay, RG2 glioma cells, with 1% FCS, with shark, rabbit and dogs 1 and 2 seeds, autoclaved

|  | no tx | 20 μl | 10 μl | 1 μl | 20 μl | 10 μl | 1 μl |
|---|---|---|---|---|---|---|---|
|  |  | Shark Seeds | | | Dog 1 seeds | | |
|  | 0.64 | 0.342 | 0.447 | 0.664 | 0.675 | 0.773 | 0.658 |
|  | 0.694 | 0.344 | 0.616 | 0.596 | 0.633 | 0.705 | 0.598 |
|  | 0.667 | 0.373 | 0.407 | 0.595 | 0.527 | 0.662 | 0.496 |
|  | 0.678 | 0.322 | 0.499 | 0.676 | 0.57 | 0.613 | 0.496 |
|  | 0.675 |  |  |  | 0.626 | 0.63 | 0.496 |
|  |  |  |  |  | 0.634 | 0.728 | 0.496 |
|  |  |  |  |  | 0.689 | 0.675 | 0.496 |
|  |  |  |  |  | 0.6 | 0.703 | 0.573 |
|  |  |  |  |  | 0.596 | 0.719 | 0.629 |
| Ab. Av. | 0.6708 | 0.34525 | 0.49225 | 0.6345 | 0.63525 | 0.67375 | 0.644375 |
| St. Dv. | 0.019817 | 0.020998016 | 0.090691326 | 0.038097619 | 0.07015035 | 0.05268437 | 0.03923168 |

|  | 20 μl | 10 μl | 1 μl | 20 μl | 10 μl | 1 μl | stauro 1% FCS |
|---|---|---|---|---|---|---|---|
|  | Dog 2 seeds | | | Rabbit Seeds | | |  |
|  | 0.555 | 0.595 | 0.687 | 0.503 | 0.62 | 0.732 | 0.108 |
|  | 0.568 | 0.642 | 0.541 | 0.522 | 0.577 | 0.676 | 0.095 |
|  | 0.543 | 0.65 | 0.601 | 0.476 | 0.607 | 0.589 | 0.093 |
|  | 0.529 | 0.648 | 0.534 | 0.512 | 0.6 | 0.647 |  |
|  | 0.561 | 0.53 | 0.66 | 0.585 | 0.564 | 0.64 |  |
|  | 0.526 | 0.638 | 0.623 | 0.584 | 0.604 | 0.61 |  |
|  | 0.498 | 0.593 | 0.644 | 0.565 | 0.519 | 0.634 |  |
|  | 0.566 | 0.658 | 0.559 | 0.536 | 0.554 | 0.649 |  |

TABLE 7-continued

MTT assay, RG2 glioma cells, with 1% FCS, with shark, rabbit and dogs 1 and 2 seeds, autoclaved

| | | | | | | | |
|---|---|---|---|---|---|---|---|
| Ab. Av. | 0.54325 | 0.61925 | 0.606125 | 0.542875 | 0.580625 | 0.647125 | 0.09866667 |
| St. Dv. | 0.024294326 | 0.04372887 | 0.05713752 | 0.0423402 | 0.03372976 | 0.0431292 | 0.00814453 |

Similar studies were carried out comparing the effect of shark PNCs with staurosporine. See Tables 8-10, below. A significant decrease in cell viability was observed for cultured cells incubated with PNCs for 20 hours (FIG. 4A). The viability of the rat and mouse glioma cells declined by 90% and 75%, respectively, while the viability of the rat ostrocytes decreased by only 25% at the same conditions. Post-exposure morphological observations of cells under optical dark-field microscope showed signs of cell death. Cells were shrunk and rounded, nuclei were condensed and showed budding of cell bodies (FIG. 4B-2). Cell damage produced by the shark PNCs compares well with the injury made by 1 μM of straurosporine (a potent apoptosis-inducing reagent) (FIG. 4B-3). A significant effect on cell viability was also observed with Hs683 (human brain glioma), H9c2[2-1](rat heart myocardium), 27FR (rat skin fibroblast), and SVGp12 (human brain astroglia) cells. Proteons and PNCs obtained from the blood plasma of healthy dog and rabbit also significantly affected the viability of the cultured mammalian cells.

FIG. 4C shows the viability of RG2 glioma cells exposed to PNCs from different sources. It takes about $1 \times 10^{12}$ PNC/ml to fully suppress these glioma cells. This concentration accounts for not more than 10% of the full concentration of PNCs in a healthy animal.

TABLE 8

MTT assay on various cell lines with shark seeds and 0% FCS

| | RG2 | | | | Fibroblast | | | | Myocard | | | |
|---|---|---|---|---|---|---|---|---|---|---|---|---|
| | No tx | 1 μl | 10 μl | 20 μl | No tx | 1 μl | 10 μl | 20 μl | No tx | 1 μl | 10 μl | 20 μl |
| Plate 1 0% FCS | 1.075 | 0.964 | 0.856 | 0.597 | 0.658 | 0.503 | 0.595 | 0.342 | 0.509 | 0.452 | 0.496 | 0.376 |
| | 1.169 | 1.014 | 0.791 | 0.496 | 0.603 | 0.517 | 0.541 | 0.36 | 0.462 | 0.373 | 0.471 | 0.382 |
| | 1.103 | 1.016 | 0.688 | 0.523 | 0.558 | 0.556 | 0.492 | 0.375 | 0.494 | 0.438 | 0.462 | 0.33 |
| | 1.084 | 1.082 | 0.739 | 0.55 | 0.556 | 0.569 | 0.432 | 0.382 | 0.449 | 0.446 | 0.513 | 0.309 |
| Ab. Av. | 1.10775 | 1.019 | 0.7685 | 0.5415 | 0.59375 | 0.53625 | 0.515 | 0.36475 | 0.4785 | 0.42725 | 0.4855 | 0.34925 |
| St. Dv. | 0.042469 | 0.048401 | 0.07191 | 0.04307 | 0.048016 | 0.031298 | 0.069508 | 0.017727 | 0.027767 | 0.036619 | 0.023302 | 0.035491 |

| | CTX astrocytes | | | | SVG astrocytes | | | | F98 glioma | | | |
|---|---|---|---|---|---|---|---|---|---|---|---|---|
| | No tx | 1 μl | 10 μl | 20 μl | No tx | 1 μl | 10 μl | 20 μl | No tx | 1 μl | 10 μl | 20 μl |
| Plate 1 0% FCS | 0.622 | 0.596 | 0.555 | 0.429 | 0.678 | 0.688 | 0.441 | 0.275 | 1.045 | 0.914 | 0.367 | 0.213 |
| | 0.603 | 0.589 | 0.559 | 0.489 | 0.681 | 05.85 | 0.439 | 0.275 | 0.977 | 0.697 | 0.444 | 0.16 |
| | 0.59 | 06.645 | 0.561 | 0.396 | 0.676 | 0.587 | 0.462 | 0.251 | 0.966 | 0.643 | 0.415 | 0.196 |
| | 0.565 | 0.6 | 0.533 | 0.434 | 0.656 | 0.667 | 0.363 | 0.244 | 1.064 | 0.73 | 0.504 | 0.172 |
| Ab. Av. | 0.595 | 0.6075 | 0.552 | 0.42725 | 0.67275 | 0.63175 | 0.42625 | 0.26125 | 1.013 | 0.746 | 0.4325 | 0.18525 |
| St. Dv. | 0.02393 | 0.02541 | 0.01291 | 0.038549 | 0.011354 | 0.053525 | 0.043431 | 0.016132 | 0.048751 | 0.117601 | 0.057274 | 0.023796 |

TABLE 9

MTT assay on various cell lines with shark seeds and 1% FCS

| | RG2 | | | | Fibroblast | | | | Myocard | | | |
|---|---|---|---|---|---|---|---|---|---|---|---|---|
| Plate 2 | No tx | 1 μl | 10 μl | 20 μl | No tx | 1 μl | 10 μl | 20 μl | No tx | 1 μl | 10 μl | 20 μl |
| 1% FCS | 0.839 | 0.606 | 0.536 | 0.36 | 0.503 | 0.44 | 0.5 | 0.307 | 0.404 | 0.43 | 0.317 | 0.317 |
| | 0.734 | 0.551 | 0.723 | 0.419 | 0.475 | 0.452 | 0.44 | 0.316 | 0.43 | 0.444 | 0.349 | 0.326 |
| | 0.634 | 0.595 | 0.551 | 0.435 | 0.465 | 0.518 | 0.351 | 0.298 | 0.408 | 0.466 | 0.326 | 0.289 |
| | 0.723 | 0.656 | 0.564 | 0.445 | 0.457 | 0.547 | 0.308 | 0.371 | 0.425 | 0.458 | 0.321 | 0.377 |

TABLE 9-continued

MTT assay on various cell lines with shark seeds and 1% FCS

| | | | | | | | | | | | | |
|---|---|---|---|---|---|---|---|---|---|---|---|---|
| Ab. Av. | 0.74025 | 0.602 | 0.5935 | 0.41475 | 0.475 | 0.48925 | 0.39975 | 0.323 | 0.41675 | 0.4495 | 0.32825 | 0.32725 |
| St. Dv. | 0.072459 | 0.043135 | 0.087088 | 0.038038 | 0.020067 | 0.051558 | 0.086535 | 0.032833 | 0.012685 | 0.015864 | 0.014315 | 0.036719 |

| | CTX astrocytes | | | | SVG astrocytes | | | | F98 glioma | | | |
|---|---|---|---|---|---|---|---|---|---|---|---|---|
| Plate 2 | No tx | 1 μl | 10 μl | 20 μl | No tx | 1 μl | 10 μl | 20 μl | No tx | 1 μl | 10 μl | 20 μl |
| 1% FCS | 0.521 | 0.501 | 0.501 | 0.355 | 0.602 | 0.509 | 0.352 | 0.248 | 0.746 | 0.687 | 0.376 | 0.137 |
| | 0.507 | 0.564 | 0.526 | 0.415 | 0.497 | 0.496 | 0.37 | 0.238 | 0.971 | 0.524 | 0.334 | 0.154 |
| | 0.542 | 0.562 | 0.42 | 0.387 | 0.534 | 0.488 | 0.401 | 0.246 | 0.91 | 1.267 | 0.283 | 0.141 |
| | 0.538 | 0.641 | 0.439 | 0.471 | 0.48 | 0.547 | 0.394 | 0.26 | 0.864 | 0.521 | 0.309 | 0.139 |
| Ab. Av. | 0.527 | 0.567 | 0.4465 | 0.407 | 0.55325 | 0.51 | 0.37925 | 0.248 | 0.87275 | 0.74975 | 0.3255 | 0.14275 |
| St. Dv. | 0.016145 | 0.057347 | 0.037189 | 0.049207 | 0.057812 | 0.026141 | 0.0225 | 0.009092 | 0.095189 | 0.353447 | 0.039585 | 0.007676 |

TABLE 10

MTT Assay on various cell lines with Staurosproine

| Saurosp | RG2 100 nm | RG2 | Fibro | Fibro | Myocard | myocard | CTX astro |
|---|---|---|---|---|---|---|---|
| Shark 7 | 0.305 | 0.12 | 0.257 | 0.168 | 0.402 | 0.154 | 0.252 |
| | 0.301 | 0.119 | 0.275 | 0.166 | 0.373 | 0.151 | 0.518 |
| Plate 3 | 0.279 | 0.119 | 0.275 | 0.171 | 0.172 | 0.159 | 0.533 |
| 1% FCS | 0.272 | 0.149 | 0.296 | 0.171 | 0.185 | 0.176 | 0.21 |
| Ab. Av. | 0.28925 | 0.12675 | 0.27575 | 0.169 | 0.283 | 0.16 | 0.37825 |
| St. Dv. | 0.016215 | 0.014841 | 0.015945 | 0.002449 | 0.121362 | 0.011165 | 0.171002 |

| Saurosp | CTX astro | SVG astro | SVG astro | F98 glioma | F98 glioma |
|---|---|---|---|---|---|
| Shark 7 | 0.212 | 0.128 | 0.067 | 0.136 | 0.108 |
| | 0.122 | 0.12 | 0.066 | | |
| Plate 3 | 0.118 | 0.128 | 0.067 | | |
| 1% FCS | 0.126 | 0.136 | 0.068 | | |
| Ab. Av. | 0.1445 | 0.128 | 0.067 | 0.13325 | 0.1085 |
| St. Dv. | 0.045118 | 0.006532 | 0.000816 | 0.008921 | 0.000577 |

Example 8

Cyclic Amplification of Proteons

A progressively increased number of proteons can be produced from plasma subjected to increasing temperatures. To examine a method of cyclic amplification, seven 1 ml samples of plasma were prepared for cyclic amplification. After the initial number of proteons was quantitated by a dark-field microscope, the first sample was incubated for 15 minutes at 65° C. and normal pressure. Five μl of the treated first sample was introduced to seed the untreated second sample, and the second sample was incubated for 15 minutes at 65° C. and normal pressure. This step was repeated: 5 μl of the second amplified sample was added to the third untreated sample. This process was repeated up to 6 cycles. A control series was run by adding of five μl of purified water (instead of seeds) to 1 ml of untreated plasma.

The first two cycles resulted in a small but significant ($p>0.001$) increase of proteon population, whereas the third cycle brought about a dramatic increase in the number of proteons. The next three cycles resulted in saturation of the proteon population. In contrast, the control samples showed no dramatic increase of proteon population. See FIG. 2.

Example 9

Comparison with Other Biological Particles

Experiments were carried out to compare the proteons obtained by the procedure described in the Example 1 with nanobacteria isolated from blood by Kajander et al. (1996) *Mol. Biol. Cell* 7:3007-3007 using the NANOCAPTURE™ enzyme linked immunosorbent assay (ELISA) kit for detection of nanobacterial antigens (Nanobac OY, Finland). The nanobacteria included in the NANOCAPTURE™ ELISA kit were used as a positive control. The BIO-RAD MICROPLATE MANAGER™ 4.01 software (Bio-Rad Labs. Inc.) was used to obtain the results of the ELISA. The assay procedure was carried out following the manufacturer's recommendations. The reaction was considered to be positive when the absorbance was significantly higher then the level of noise. Results of interaction of antibodies grown against nanobacteria with proteons and plasma are summarized in Table 11.

TABLE 11

Interaction of antibodies specific to nanobacteria with proteons and plasma.

| No | Sample | Condition | Reaction |
|---|---|---|---|
| 1 | Proteons, human 1 | Freshly prepared at 120° C. and 20 psi, 2 h | − |
| 2 | Proteons, human 2 | Freshly prepared at 120° C. and 20 psi, 2 h | − |
| 3 | Proteons, rabbit | Freshly prepared at 120° C. and 20 psi, 2 h | − |
| 4 | Proteons, human 1 | Incubated 13 days, 37° C. after preparation | − |
| 5 | Proteons, human | Freshly prepared | − |
| 6 | Plasma, human 1 | Incubated 13 days, 37° C. | − |
| 7 | Proteons, human 1, in D5648[a] | Incubated 13 days, 37° C. | + |
| 8 | Proteons human 1, in D6429[b] | Incubated 13 days, 37° C. | + |
| 9 | Plasma, human 1 in D5648[a] | Incubated 13 days, 37° C. | + |
| 10 | Plasma, human 1, in D6429[b] | Incubated 13 days, 37° C. | + |
| 11 | Proteons, human 1, in D5648[a] | Incubated 13 days, 37° C., 5% $CO_2$-95% air | + |
| 12 | Proteons, human 1, in D6429[b] | Incubated 13 days, 37° C., 5% $CO_2$-95% air | + |
| 13 | Plasma, human 1, in D5648[a] | Incubated 13 days, 37° C., 5% $CO_2$-95% air | + |
| 14 | Plasma, human 1, in D6429[b] | Incubated 13 days, 37° C., 5% $CO_2$-95% air | + |
| 15 | Proteons, human 1, in D5648[a] | Incubated 13 days, 37° C., 5% $CO_2$-95% air | + |
|  | D5648[a] | Incubated 13 days, 37° C. | + |
|  | D6429[b] | Incubated 13 days, 37° C. | + |
| 16 | D6429[b] | Freshly Prepared | − |
| 17 | Water[c] | Freshly Prepared | − |
| 18 | Broth[d] | 120° C. and 20 psi, 2 h | − |
|  | Nanobacteria |  | + |

[a]D5648 tissue culture media (Sigma) with 10% FBS (HyClone).
[b]D6429 tissue culture media (Sigma) with 10% FBS (HyClone).
[c]Purified water (Direct QTM, Millipore, 17 MOhm)
[d]LB-Medium (BIO 101, Inc.; 10 g Trypton-B, 5 g yeast extract-B, 10 h NaCl in 1 L of water).

Nanobacteria gave a positive signal, while all freshly prepared proteons, showed no interaction. Proteons incubated in cell culture media for 13 days, at 37° C. (with and without $CO_2$) show a positive reaction. However, the culture media alone incubated for 13 days, at 37° C. also gave a positive reaction, while freshly prepared culture media was negative, indicating that nanobacterial antigen appeared from the culture media during the incubation.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

All publications and patent applications mentioned in the specification are indicative of the level of those skilled in the art which this invention pertains. All publications and patent applications are herein incorporated by reference to the same extent as if each individual publication or patent application was specifically and individually indicated to be incorporated by reference.

Those skilled in the art will recognize, or be able to ascertain using no more than routine experimentation, many equivalents to the specific embodiments of the invention described herein, Such equivalents are intended to be encompassed by the following claims.

That is claimed is:

1. A method for detecting misfolded proteins that bind to proteon nucleation centers (PNCs) and aggregate to form proteons in a biological sample comprising:
   a) contacting the biological sample with isolated proteon nucleation centers (PNCs), wherein the PNCs comprise metallic nanoparticles that have a diameter of about 1-2 nm and about 40-300 metal atoms selected from the group consisting of copper, zinc, iron and alloys of copper, zinc or iron, and wherein the misfolded proteins bind the PNCs and aggregate to form proteons; and
   b) detecting the proteons formed in the sample, thereby detecting the misfolded proteins in the biological sample,
   wherein the biological sample is blood or plasma.

2. The method of claim 1, wherein the proteons formed comprise misfolded prion proteins.

3. The method of claim 1, wherein the proteons formed are detected with a labeled antibody.

4. A method for detecting misfolded proteins that bind to proteon nucleation centers (PNCs) and aggregate to form proteons in a biological sample comprising:
   a) adding to the biological sample isolated proteon nucleation centers (PNCs), wherein the PNCs comprise metallic nanoparticles having a diameter of about 1-2 nm and about 40-300 metal atoms selected from the group consisting of copper, zinc, iron and alloys of copper, zinc or iron, and wherein the misfolded proteins bind the PNCs and aggregate to form proteons;
   b) heating the biological sample to amplify the concentration of proteons; and
   c) detecting the proteons formed in the biological sample, thereby detecting the misfolded proteins in the biological sample,
   wherein the biological sample is blood or plasma.

5. The method of claim 4, wherein the sample is heated for at least about 1, 5, 10, 15, 20, 25, 30, 35, 40, 45, 50, 55, 60, 65, 70, 75, 80, 85, 90, 95, 100, 105, 110, 115, or 120 minutes.

6. The method of claim 4, wherein the sample is heated to a temperature of at least 37, 40, 45, 50, 55, 60, 65, 70, 75, 80, 85, 90, 95, 100, 105, 110, 115, or 120° C.

7. The method of claim 4, further comprising applying pressure to the sample of at least 14, 15, 16, 17, 18, 19, 20, 21, 22, 23, 24 or 25 psi.

8. The method of claim 4, wherein the proteons formed comprise misfolded prion proteins.

9. The method of claim 4, wherein the proteons formed are detected with a labeled antibody.

10. A method for detecting misfolded proteins that bind to proteon nucleation centers (PNCs) and aggregate to form proteons in a biological sample, wherein the biological sample is blood or plasma, the method comprising:
    a) adding to the biological sample isolated proteon nucleation centers (PNCs), wherein the PNCs comprise metallic nanoparticles having a diameter of about 1-2 nm and about 40-300 metal atoms selected from the group consisting of copper, zinc, iron and alloys of copper, zinc or iron, and wherein the misfolded proteins bind the PNCs and aggregate to form proteons;
    b) heating the biological sample for amplification of the proteons;
    c) repeating steps a) and b); and
    d) detecting the proteons formed in the biological sample, thereby detecting the misfolded proteins in the biological sample.

11. The method of claim 10, wherein steps (a) and (b) are repeated until the number of proteons formed in the sample no longer increases.

12. The method of claim 10, wherein the sample is heated for at least about 1, 5, 10, 15, 20, 25, 30, 35, 40, 45, 50, 55, 60, 65, 70, 75, 80, 85, 90, 95, 100, 105, 110, 115, or 120 minutes.

13. The method of claim 10, wherein the sample is heated to a temperature of at least 37, 40, 45, 50, 55, 60, 65, 70, 75, 80, 85, 90, 95, 100, 105, 110, 115, or 120° C.

14. The method of claim 10, further comprising applying pressure to the sample of at least 14, 15, 16, 17, 18, 19, 20, 21, 22, 23, 24 or 25 psi.

15. The method of claim 10, wherein the sample is heated for at least 15 minutes at a temperature of at least 60° C. and steps a) and b) are repeated at least six times.

16. The method of claim 10, wherein the proteons formed comprise misfolded prion proteins.

17. The method of claim 10, wherein the proteons formed are detected with a labeled antibody.

* * * * *

SEQUENCE LISTING

<160> NUMBER OF SEQ ID NOS: 1

<210> SEQ ID NO 1
<211> LENGTH: 10
<212> TYPE: PRT
<213> ORGANISM: Artificial
<220> FEATURE:
<223> OTHER INFORMATION: Partial Sequence Showing Homology with Rabbit
      Alpha Chain of Hemoglobin
<220> FEATURE:

-continued

```
<221> NAME/KEY: Xaa
<222> LOCATION: (6)..(6)
<223> OTHER INFORMATION: "Xaa" in position #6 is D or E
<220> FEATURE:
<221> NAME/KEY: Xaa
<222> LOCATION: (7)..(7)
<223> OTHER INFORMATION: "Xaa" in position #7 is E or K
<220> FEATURE:
<221> NAME/KEY: Xaa
<222> LOCATION: (10)..(10)
<223> OTHER INFORMATION: "Xaa" in position #10 is A or I

<400> SEQUENCE: 1

Val Leu Ser Pro Ala Xaa Xaa Thr Asn Xaa
1               5                   10
```